(12) United States Patent
Miller et al.

(10) Patent No.: US 12,354,262 B2
(45) Date of Patent: Jul. 8, 2025

(54) MULTI-RESOLUTION SEGMENTATION FOR GIGAPIXEL IMAGES

(71) Applicant: Leica Biosystems Imaging, Inc., Vista, CA (US)

(72) Inventors: Derek Miller, Oceanside, CA (US); Chad Salinas, San Diego, CA (US)

(73) Assignee: Leica Biosystems Imaging, Inc., Vista, CA (US)

( * ) Notice: Subject to any disclaimer, the term of this patent is extended or adjusted under 35 U.S.C. 154(b) by 411 days.

(21) Appl. No.: 18/082,406

(22) Filed: Dec. 15, 2022

(65) Prior Publication Data

US 2023/0245303 A1 Aug. 3, 2023

Related U.S. Application Data

(60) Provisional application No. 63/305,182, filed on Jan. 31, 2022.

(51) Int. Cl.
*G06V 10/764* (2022.01)
*G06T 3/4053* (2024.01)
(Continued)

(52) U.S. Cl.
CPC .......... *G06T 7/0012* (2013.01); *G06T 3/4053* (2013.01); *G06V 10/44* (2022.01);
(Continued)

(58) Field of Classification Search
None
See application file for complete search history.

(56) References Cited

U.S. PATENT DOCUMENTS 9,412,162 B2 * 8/2016 Molin .................... G06T 3/4053
2012/0086850 A1 * 4/2012 Irani ......................... G06T 3/40
348/E7.003

(Continued)

OTHER PUBLICATIONS

Gu, Feng, et al. "Multi-resolution networks for semantic segmentation in whole slide images." *Computational Pathology and Ophthalmic Medical Image Analysis: First International Workshop, COMPAY 2018, and 5th International Workshop, OMIA 2018, Held in Conjunction with MICCAI 2018*, Granada, Spain, Sep. 16-20, 2018, Proceedings 5. Springer International Publishing, 2018.
(Continued)

*Primary Examiner* — Tsung Yin Tsai
(74) *Attorney, Agent, or Firm* — FROST BROWN TODD LLP

(57) ABSTRACT

Systems and methods for determining pixel classification information using images depicting at least a portion of a whole slide image (WSI) of a stained tissue sample. A system can store a first image of the tissue sample at a first resolution, a second image of the tissue sample at a second resolution that is higher than the first resolution, and a third image of the tissue sample at a third resolution that is higher than the second resolution, the first, second, and third images depicting at least a portion of a same area of the tissue sample. The system can include be configured to generate first feature information based on the first image, generate second feature information based on the second image, and determine pixel classification information of at least a portion of the WSI based on the third image, the first feature information and second feature information.

20 Claims, 15 Drawing Sheets

(51) Int. Cl.
    *G06T 7/00*   (2017.01)
    *G06V 10/44*  (2022.01)
    *G06V 10/82*  (2022.01)
(52) U.S. Cl.
    CPC ............ *G06V 10/764* (2022.01); *G06V 10/82* (2022.01); *G06T 2207/20016* (2013.01); *G06T 2207/30024* (2013.01)

(56) References Cited

U.S. PATENT DOCUMENTS

| | | | | |
|---|---|---|---|---|
| 2015/0055844 | A1* | 2/2015 | Molin | G06T 3/4053 382/131 |
| 2018/0232883 | A1* | 8/2018 | Sethi | G16H 30/40 |
| 2018/0286043 | A1* | 10/2018 | Barnes | G01N 33/4833 |
| 2019/0355113 | A1* | 11/2019 | Wirch | G06T 7/32 |
| 2022/0138955 | A1* | 5/2022 | Laurinavicius | G06T 7/13 382/133 |
| 2023/0177682 | A1* | 6/2023 | Xiao | G06T 7/11 382/133 |
| 2023/0178221 | A1* | 6/2023 | Miri | G16H 30/40 382/128 |

OTHER PUBLICATIONS

Mehta, Sachin, et al. "Learning to segment breast biopsy whole slide images." *2018 IEEE Winter Conference on Applications of Computer Vision (WACV)*. IEEE, 2018.

Extended European Search Report dated Jun. 13, 2023, for Application No. 22214152.5, 14 pages.

Van Rijthoven, Mart, et al. "HookNet: Multi-resolution convolutional neural networks for semantic segmentation in histopathology whole-slide images." *Medical image analysis* 68 (2021): 101890.

\* cited by examiner

MULTI-RESOLUTION SEGMENTATION FOR GIGAPIXEL IMAGES

PRIORITY

This document claims priority to U.S. Provisional Patent App. No. 63/305,182, entitled "Multi-Resolution Segmentation for Gigpixel Images," filed on Jan. 31, 2022, the disclosure of which is incorporated by reference herein.

BACKGROUND

Technical Field

The described technology relates to semantic segmentation of features in images, and in particular semantic segmentation performed using multi-resolution images derived from stained whole slide pathology images.

SUMMARY

The systems, methods, and devices described herein each have several aspects, no single one of which is solely responsible for its desirable attributes. Without limiting the scope of this disclosure, several non-limiting features will now be discussed briefly. The methods and techniques described herein relate to systems and methods for determining feature information from multiscale images derived from a whole slide image (WSI) of a tissue sample. The systems and methods can use machine learning to train a system architecture having multiple encoder-decoders. Each encoder-decoder can be trained separately on images of a certain resolution to determine feature information and for semantic segmentation of images of that (or a similar) resolution. Each of the encoder-decoders can provide feature information that it generates to another encoder-decoder that is processing images of a higher resolution.

One innovation includes an apparatus for determining pixel classification information using a set of images depicting at least some of a whole slide image (WSI) of a stained tissue sample. In one example, the apparatus includes a non-transitory computer storage medium configured to store executable instructions, a first context image of the tissue sample at a first resolution, a second context image of the tissue sample at a second resolution that is higher than the first resolution, and a target image of the tissue sample at a third resolution that is higher than the second resolution, and optionally one or more additional context images n where n is an integer, wherein when n=1 the additional context image 1 has a resolution higher than the resolution of the second context image, wherein when n>1 each additional context image n has a resolution higher than the resolution of the additional image n−1, and wherein the first context image, second context image, target image, and each additional image n depict at least a portion of a same area of the tissue sample; one or more hardware processors in communication with the computer storage medium, wherein the executable instructions, when executed by the one or more hardware processors, configure the one or more hardware processors to generate first feature information based on the first image; generate second feature information based on the second image; generate additional feature information n separately for each additional image n; and determine pixel classification information of at least a portion of the WSI based on the target image, the first feature information, the second feature information, and each additional feature information n.

Another innovation includes a non-transitory computer readable medium for determining pixel classification of at least a portion of a whole slide image (WSI) using a set of images depicting at least a portion of the WSI, the computer readable medium having program instructions for causing a hardware processor to perform a method of receiving a set of images including a first context image of the tissue sample at a first resolution, a second context image of the tissue sample at a second resolution that is higher than the first resolution, a target image of the tissue sample at a third resolution that is higher than the second resolution, and optionally one or more additional context images n where n is an integer, wherein when n=1 the additional context image 1 has a resolution higher than the resolution of the second context image, wherein when n>1 each additional context image n has a resolution higher than the resolution of the additional image n−1, and wherein the first context image, second context image, target image, and each additional image n depict at least a portion of a same area of the tissue sample; generate first feature information based on the first image; generating second feature information based on the second image; generating additional feature information n separately for each additional image n; and determining pixel classification information of at least a portion of the WSI based on the target image, the first feature information, the second feature information, and each additional feature information n.

Another innovation includes a method for receiving a set of images including a first context image of the tissue sample at a first resolution, a second context image of the tissue sample at a second resolution that is higher than the first resolution, a target image of the tissue sample at a third resolution that is higher than the second resolution, and optionally one or more additional context images n where n is an integer, wherein when n=1 the additional context image 1 has a resolution higher than the resolution of the second context image, wherein when n>1 each additional context image n has a resolution higher than the resolution of the additional image n−1, and wherein the first context image, second context image, target image, and each additional image n depict at least a portion of a same area of the tissue sample; generating first feature information based on the first image; generating second feature information based on the second image; generating additional feature information n separately for each additional image n; and determining pixel classification information of at least a portion of the WSI based on the target image, the first feature information, the second feature information, and each additional feature information n, wherein the method is performed by one or more computer hardware processors executing program instructions stored on a non-transitory computer medium.

BRIEF DESCRIPTION OF THE DRAWINGS

The features and advantages of the systems and methods described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. The drawings may not be drawn to scale.

DETAILED DESCRIPTION OF CERTAIN INVENTIVE ASPECTS

Figure 1:
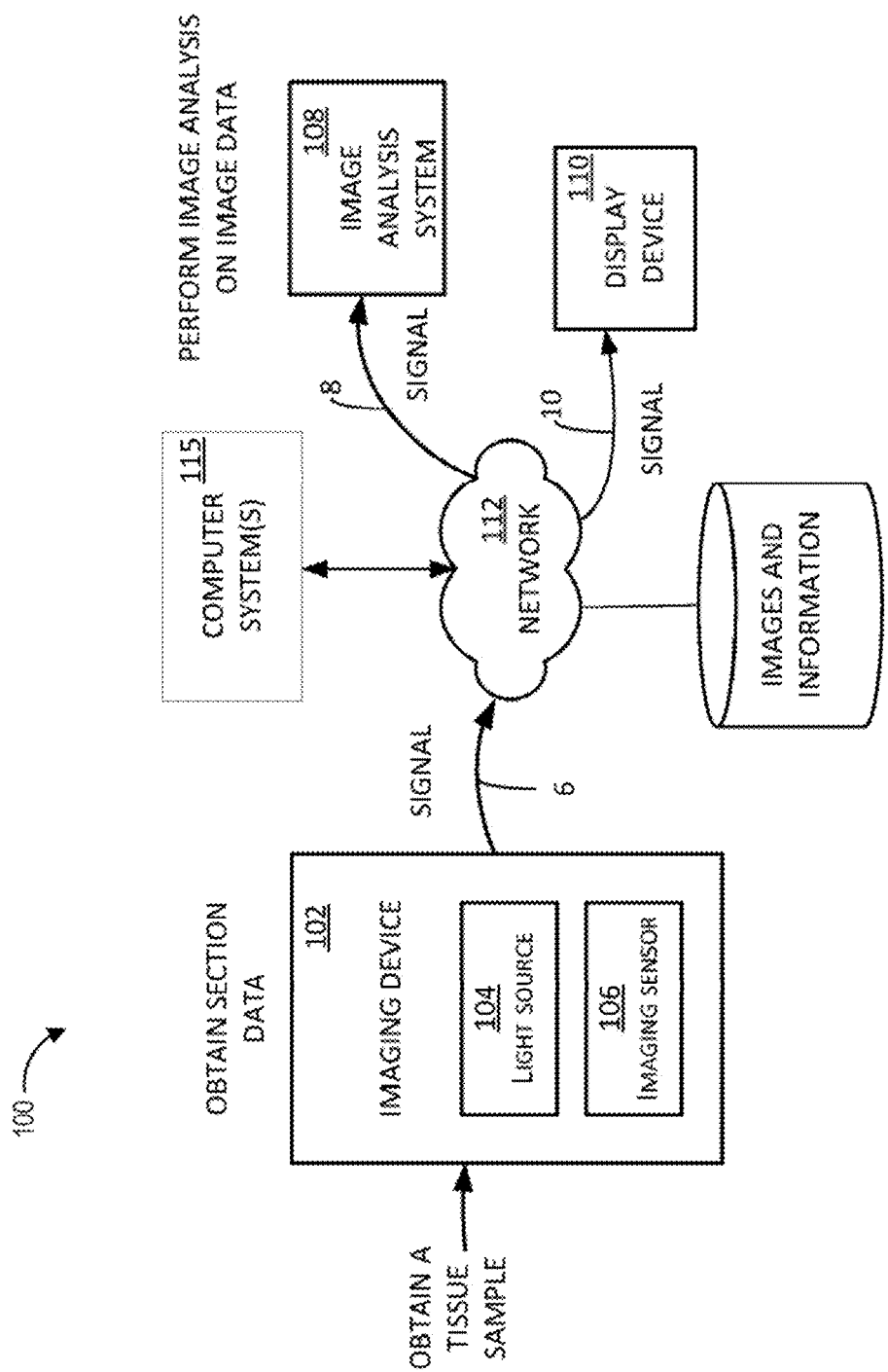
FIG. 1 illustrates an example environment of an imaging system which includes an image analysis system that can be used to implement the systems and methods described herein.

Tissue samples are routinely analyzed microscopically for various diagnostic purposes, including detecting cancer by identifying structural abnormalities in the tissue samples. Various tissue structure and/or structural abnormalities ("features") in a tissue sample may be determined by image processing techniques performed on digitized representations of the tissue sample. One such image processing technique is semantic image segmentation, which partitions pixels of an image into coherent parts in order to simplify image representation and understanding. In medical imaging, tumor detection and segmentation are necessary steps for diagnosis and disease characterization. This is particularly important in histopathology, where tissue samples which may include a variety and number of cells having one or more coherencies need to be analyzed by pathologists for diagnostic purposes. In digital pathology, a digitized body tissue sample can be analyzed for diagnostic or forensic purposes, including a whole-slide images (WSI). Exemplary digital whole slide images include a large number of pixels, such as at least one billion pixels (a gigapixel). A downside of using high-resolution images (such as gigapixel images) in digital pathology is that processing the entire image or large portions of the image may be impractical due to computational and/or memory resource limitations. Generally, high-resolution images (such as gigapixel images) are too large to be processed by a graphics processing unit (GPU) or another processor all at once.

Individual cancer cells may share morphological characteristics. As an example, in hematoxylin and eosin (H&E) stained tissue samples, different histological types of cancer can be distinguished. To differentiate between types of cancer, pathologists can observe and analyze a zoomed-in (i.e., more detailed, higher resolution images) of a tissue sample and a zoomed-out (i.e., more context, lower resolution images). The higher resolution images provide details of structure of individual cells and groups of cells. The lower resolution images provide context of the cells in the tissue sample, which can be impossible to determine from the higher resolution images because of the smaller actual area of the tissue sample they depict. The lower resolution image can depict the same portion (or area) of the tissue sample as the high resolution image, and can also show an additional portion of the tissue sample (that is not shown in the high resolution image) that is on at least one side of a high resolution image, which provides context for the analysis of cells in the tissue sample. Accordingly, instead of attempting to process a WSI as a single image, for diagnostic or classification purposes a diagnostic/classification algorithm may break the high-resolution image into smaller sized patches for more efficient/manageable processing. An exemplary algorithm breaks a high-resolution image into smaller patches, and the smaller patches are used for training/making inferences using a deep convolutional neural network. However, processing smaller sized patches in this manner breaks the continuity and overall structure present in the entire image and leads to information loss for diagnostic/classification purposes. There may be underlying biological connections among different regions in the high-resolution image that are not properly captured when the high-resolution image is divided into patches because, for example, cells indicative of a tumor region may be spread out among multiple smaller-sized patches in the image.

Figure 4A:
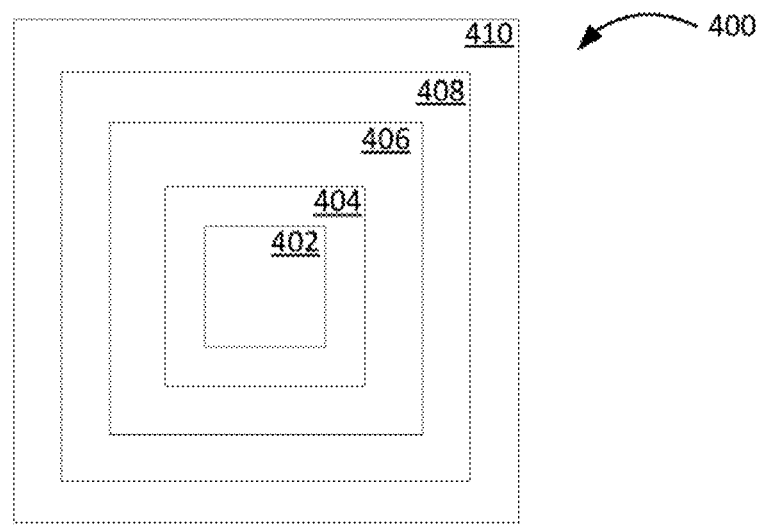
FIGS. 4A and 4B illustrate an example of multi-resolution images that can be used as input to one or more encoder-decoders.
Figure 4B:
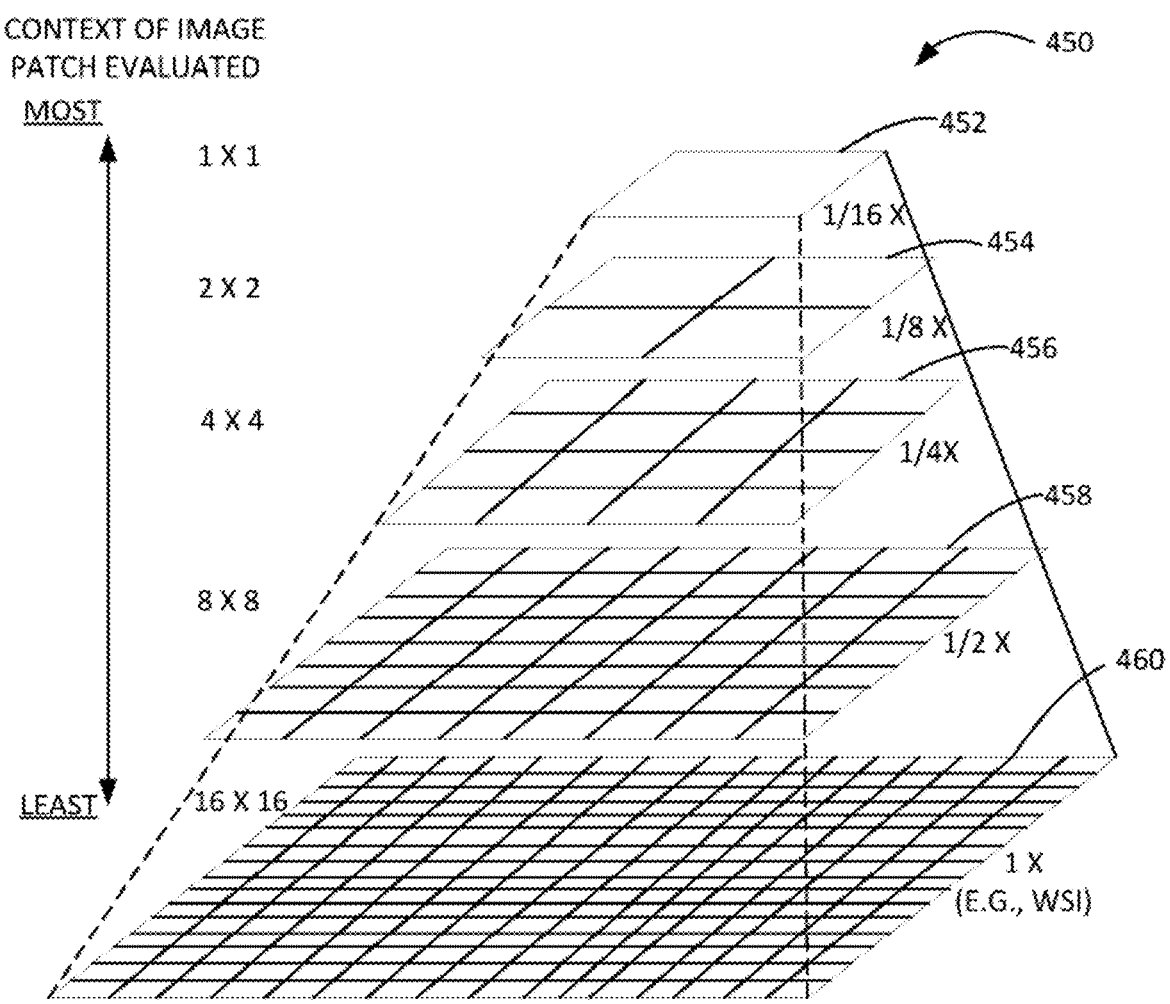
Figure 5:
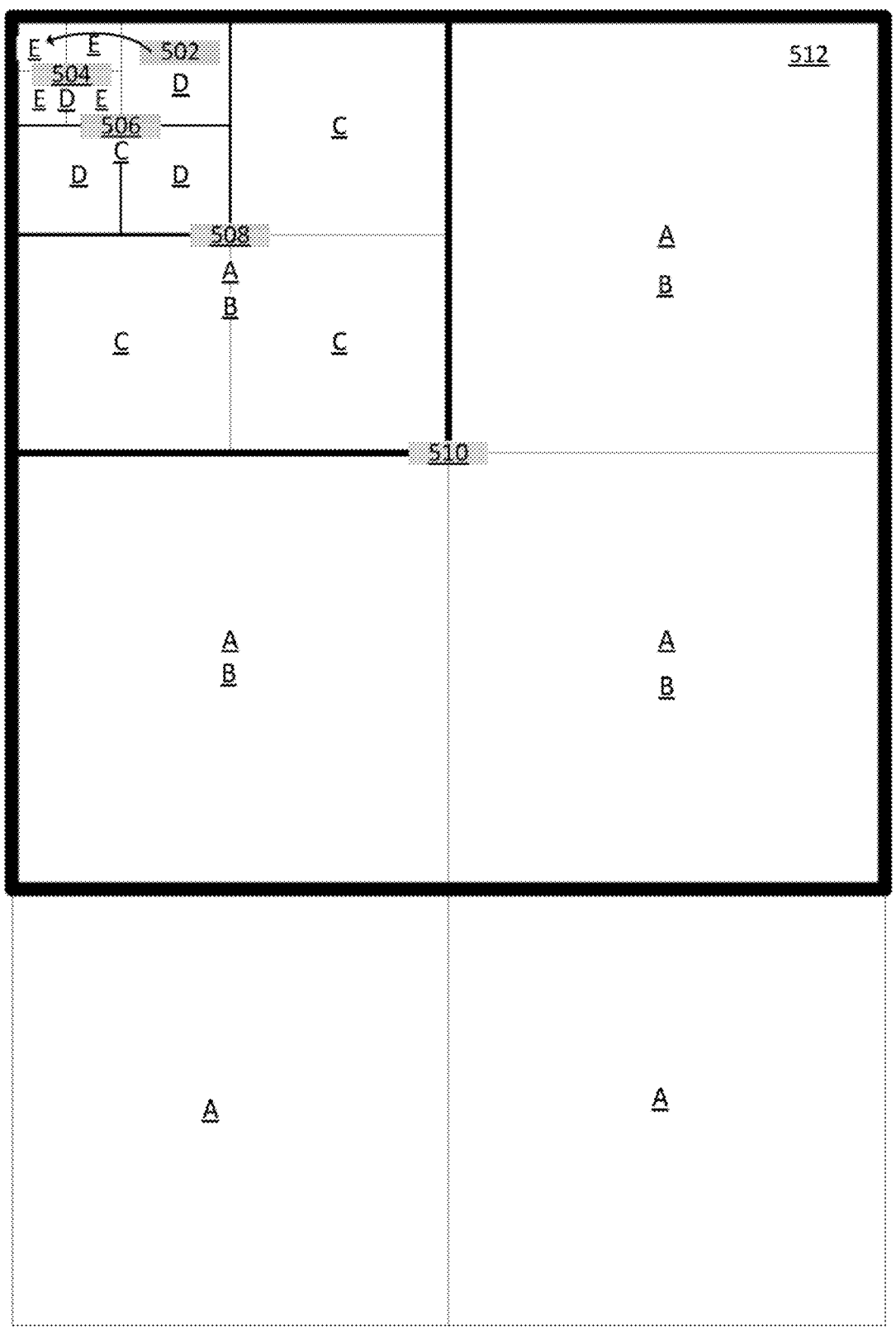
FIG. 5 illustrates another example of multi-resolution images that can be used as input to one or more encoder-decoders.

In various embodiments, a set of multi-resolution images ("MR Images") can be generated from a WSI, the set of MR Images having two or more images of different resolution such that the set of MR Images is a set of images having a hierarchy of resolutions (e.g., three, four, five or more images of different resolutions). Each lower resolution image in the hierarchy depicts the area of the tissue sample as each of the higher resolution images, and some additional area of the tissue sample. In one example, the set of MR Images can be concentric images, as illustrated in the example of FIG. 4A. In another example, the set of MR Images can be non-concentric images, as illustrated in the examples of FIGS. 4B and 5, wherein each lower resolution image of a certain resolution depicts the same area of the tissue sample as four of the next higher resolution images. In yet another example, a lower resolution image in a set of MR Images of a certain resolution depicts the same portion of the tissue sample as two or more (e.g., 2, 3, 4, 5, 6, 7, 8, 9, 10, 11, 12, 13, 14, 15, 16, 17, 18, 19, 20, 21, 22, 23, 24, or 25, or more) images of the next highest resolution. As illustrated in the examples shown in FIG. 4B and FIG. 5, for most resolutions (sometimes referred to herein as a resolution "layer" of "set"), one or more images having that resolution exist. For example, as shown in the example of FIG. 5, the set of MR Images includes four images of a first resolution in "layer" 404, 16 images of a second resolution that is higher than the first resolution in layer 406, and 64 images of a third resolution that is higher that the second resolution and the first resolution in layer 408, etc. In some embodiments, the X, Y dimensions of the images in each layer may be the same (nearly so) such that the input image size to each encoder-decoder is the same.

Systems and methods are disclosed herein that may be used to advantageously improve processing large images (e.g., WSI's) using machine learning based histopathological image classification, which can include semantic segmentation of features or other structural aspects depicted in a WSI. Some of the machine learning techniques and/or networks may be deep learning techniques and/or networks. An exemplary machine learning system described herein may include deep-learning network architecture. An exemplary machine learning system described herein can include an encoder-decoder architecture having multiple encoder-decoders. Each encoder-decoder can be based on convolutional neural networks (CNN). Each encoder-decoder can be configured and trained to process certain type of images, for example, input images of a certain size and/or input images of a certain resolution. Generally, an end-to-end network architecture leveraging machine learning training (such as deep learning) and inference can be used to address the problems associated with processing high-resolution images and maintaining semantic relationships among the patches of the high-resolution image.

In some embodiments, the encoder-decoders can be implemented as a neural network, for example, a recurrent neural network. A machine learning system may extract patches for a high-resolution image for training or classification purposes. A first portion of a machine learning model (such as a convolutional neural network) of the system may extract features for the individual patches and output a vector. A second portion of the machine learning model (such as a recurrent neural network) may extract features based on multiple patches, such that sequential and spatial aspects of the high-resolution image are represented in the output vector from the second portion of the machine learning model. Patches can be provided to a recurrent neural network in a sequential manner, and the recurrent neural network may extract features from the high-resolution image that represent sequential information that can define global properties of the image file. A third portion of the machine learning model (such as another recurrent neural network) receives the output vector from the first and second portions of the model and may provide features integrated from features obtained from previous layer(s) and output a modified feature vector. A final classification may be determined from the modified feature vectors obtained as an output from the third portion of the machine learning model. Thus, improved systems and methods for machine learning based histopathological image classification, including semantic segmentation, may process high-resolution images in an efficient manner while taking into account the sequential and spatial nature of the smaller patches from the high-resolution image.

The image processing system for semantic segmentation can include an encoder-decoder architecture having multiple encoder-decoders each trained/configured (e.g., with certain parameters/weights derived from training) to generate information relating to features, objects, or structure depicted in images derived from a WSI (referred to herein collectively as "feature information"). To perform semantic segmentation on the WSI to take advantage of images having high-resolution in other images having greater context, the encoder-decoder architecture described herein can be used.

A set of MR Images can be generated that depicts at least a portion of the WSI. Feature information generated by an encoder-decoder that is processing images of a lower resolution/higher context can be passed to another encoder decoder that is processing images of a higher resolution/lower context as an additional input, and this flow of feature information to an encoder-decoder processing images of a high-resolution can be repeated for each encoder-decoder.

As one example, a set of MR Images depicting a WSI has images of five different resolutions R1, R2, R3, R4, and R5 (or five different resolution layers R1, R2, R3, R4, and R5) where the resolution R1<R2<R3<R4<R5. Correspondingly, the context (or area) of each image of a certain resolution is the opposite (assuming the X, Y image dimensions are the same or approximately the same), where context of images of resolution R1>context of images of resolution R2>context of images of resolution R3>context of images of resolution R4>context of images of resolution R5. For examples, feature information generated by a first encoder-decoder processing images of the resolution R1 can be provided to a second encoder-decoder processing images of the resolution R2. Feature information generated by the second encoder-decoder, that is based on the images of the resolution R2 and based on feature information received from the first encoder, can be provided to a third encoder-decoder that is processing images of the resolution R3. Feature information generated by the third encoder-decoder, that is based on the images of resolution R3 and based on feature information received from the second encoder, can be provided to a fourth encoder-decoder that is processing images of the resolution R4. Feature information generated by the fourth encoder-decoder, that is based on the images of the resolution R4 and based on feature information received from the third encoder, can be provided to a fifth encoder-decoder that is processing images of the resolution R5. Outputs from one or more of the first, second, third, fourth, and fifth encoder-decoders can be used to generate semantic segmentation information for the WSI.

This hierarchical processing to determine feature information by an encoder-decoder processing images at a first resolution, and passing the feature information to an encoder-decoder processing images of a higher resolution that depict at least a portion of the lower resolution images can continue for each of the resolution levels, such that ultimately semantic segmentation results for each of the portions of the WSI can be generated based on the images at each resolution level and feature information that is generated by each of the encoder-decoders. Each encoder-decoder can be trained separately from the other encoder-decoders. Each encoder-decoder can be trained on images having the resolution (or nearly the resolution) of the images of the WSI the encoder-decoder will receive for analysis. Each encoder-decoder may be trained to produce semantic segmentation results as a "final" output at an endpoint of the encoder-decoder process. During the encoding-decoding process however, the encoder-decoder generates feature information that can be provided to another encoder-decoder processing images of a higher resolution, and which used the feature information to determine further feature information, or sematic segmentation results relating to the WSI. Using multiple encoder decoders each processing images of a different resolution allows feature information, and ultimately classification of the pixels to a class, to be generated from images having the optimal resolution for such classification. In various embodiments, the encoder-decoder architecture described herein may include numerous encoder-decoders ("encoder-decoder branches" or simply "branches") each configured (e.g., structured and trained) to process images of a certain resolution. For example, if the set of MR Images includes images of five different resolutions, an embodiment can include at least five branches, each of the at least five branches configured to process images of one of the five resolutions. In some embodiments, each branch may be implemented differently, for example, having a different number of layers. In some embodiments, each encoder-decoder branch can be an autoencoder.

In some embodiments, the encoder-decoder architecture is not constrained by a single loss function such that the context branches can be independently optimized (separately from the target branch). The intended benefit of independent optimization is that each branch can be optimized to find the features in its respective resolutions which best separate the classes for the features/objects/structure it is trying to classify. In an example, each branch can be optimized to find the features in its respective resolutions which results in the most accurate semantic segmentation. To implement this during training, the loss in each branch can be calculated starting with the highest resolution/lowest context branch, and backpropagate to update the weights of the neural network(s) used in the branch. The backpropagated loss from the feature information passed down from the larger context branches can either be added to the loss for the tensor of features in each of those models or dropped so that each branch is completely independently optimized. Then each branch's loss is just the difference between its target image and its predictions and that is backpropagated to update the weights of that branch. In other words, features (or feature information) of processed image patches is passed down from a low resolution model to a higher resolution model, and then the impact of using those features in the higher resolution model is passed back to the lower resolution model, and the lower resolution model can be updated, adding the loss calculated in the higher resolution model on the shared feature set to the loss calculated in the lower resolution model during it backpropagation on the same feature set. In some embodiments, to improve computational cost and/or run time efficiency, the largest context branches may be computed first and the set of features related to that portion of the WSI are held constant, while the higher resolution branches iterate across the largest image.

System Overview

FIG. 1 illustrates an example environment 100 in which a user and/or an imaging system may analyze a tissue sample. The environment 100 includes an automated slide stainer that is controlled to produce consistently stained slides based on one or more protocols. The environment 100 can also include an imaging device 102 that generates a digital representation of a stained slide. In some embodiments, the environment 100 includes a multi-color (or broad spectrum) imaging device 102. The imaging device 102 can be one or more of a camera, a scanner, a medical imaging device, a microscope, etc. Further, the imaging device 102 can use imaging technologies such as X-ray radiography, magnetic resonance imaging, ultrasound, endoscopy, elastography, tactile imaging, thermography, medical photography, nuclear medicine functional imaging, positron emission tomography, single-photon emission computed tomography, etc. For example, the imaging device can be a magnetic resonance imaging ("MRI") scanner, a positron emission tomography ("PET") scanner, an ultrasound imaging device, an x-ray imaging device, a computerized tomography ("CT") scanner. The digital representation may be referred to herein as an "image" and can be presented on a computer display device 110 for evaluation by a user. Although referred to as an image, the digital representation is a set of data which can be analyzed by computer processes, for example, for object (e.g., marker) identification, characterization, quantification, and/or spatial analysis of identified objects, etc. In some examples, an image can be used as training data for a machine learning process, and/or processed by a machine learning process to determine information from the image. The digital representation can be communicated as signal 6 to a network 112 and then communicated as a signal 8 to an image analysis system 108 for processing (e.g., feature detection, feature measurements, etc.). The image analysis system 108 may perform image analysis on received image data. The image analysis system 108 can normalize the image data obtained using color-stained images for input to a machine learning algorithm, which may determine characteristics of the image. The image analysis system may register and/or transform an image to align an image with other related images to facilitate analysis of information in the related images. Results from the image analysis system 108 can be communicated as a signal 10 to one or more display devices 110 (which also may be referred to herein as a "display device" or a "client device").

In some implementations, the imaging device 102 includes a light source 104 configured to emit light onto or through the tissue sample. In an example, the light source can be a broad-spectrum white light source emitting light across a spectrum of wavelengths. In another example, the light source can emit light across a particular range of one or more wavelengths. In some embodiments, the light source 104 is configured to provide a "brightfield" emitting light through the sample. In some embodiments, the light source 102 is configured to provide light of wavelengths that causes fluorescence of material (e.g., markers, objects) in the tissue sample. The imaging device 102 includes one or more imaging sensor 106 configured to detect light emitted from, or transmitted through, the tissue sample, based on the implementation. Embodiments of imaging using the light source 104 can involve providing light to the tissue sample within a range of frequencies.

In certain embodiments, the stained tissue sample may reflect light, or through fluorescence, emit light received from the light source 104, which can then be detected at the image sensor 106. In these implementations, the light source 142 and the image sensor 106 may be located on substantially the same side of the tissue sample. In other implementations, the light source 104 and the image sensor 106 may be located on opposite sides of the tissue sample. The image sensor 106 may be further configured to generate image data based on the broad-spectrum light detected at the image sensor 106. In certain implementations, the image sensor 106 may include a high-resolution sensor configured to generate a high-resolution image of the tissue sample. The high-resolution image may be generated based on excitation of the stained tissue sample in response to light provided onto the sample at different frequencies (e.g., a frequency spectrum) or different wavelengths. For example, fluorescence microscopy uses intense, near-monochromatic illumination. In some embodiments, light is provided by one or more xenon arc lamps or mercury-vapor lamps with an excitation filter, a laser, a supercontinuum source, and/or a high-power LED.

The imaging device 102 may capture and/or generate image data for analysis. The imaging device 102 may include one or more lenses, image sensors, processors, or memory components. The imaging device 102 may receive a user interaction. The user interaction may be a request to capture image data. Based on the user interaction, the imaging device 102 may capture image data. In some embodiments, the imaging device 102 may capture image data periodically (e.g., every 10, 20, or 30 minutes). In other embodiments, the imaging device 102 may determine that an item has been placed in view of the imaging device 102 (e.g., a histological sample has been placed on a table and/or platform associated with the imaging device 102) and, based on this determination, capture image data corresponding to the item. The imaging device 102 may further receive image data from additional imaging devices. For example, the imaging device 102 may be a node that routes image data from other imaging devices to the image analysis system 108. In some embodiments, the imaging device 102 may be located within the image analysis system 108. For example, the imaging device 102 may be a component of the image analysis system 108. Further, the image analysis system 108 may perform an imaging function. In other embodiments, the imaging device 102 and the image analysis system 108 may be connected (e.g., wirelessly or wired connection). For example, the imaging device 102 and the image analysis system 108 may communicate over a network 112. Further, the imaging device 102 and the image analysis system 108 may communicate over a wired connection. In one embodiment, the image analysis system 108 may include a docking station that enables the imaging device 102 to dock with the image analysis system 108. An electrical contact of the image analysis system 108 may connect with an electrical contact of the imaging device 102. The image analysis system 108 may be configured to determine when the imaging device 102 has been connected with the image analysis system 108 based at least in part on the electrical contacts of the image analysis system 108. In some embodiments, the image analysis system 108 may use one or more other sensors (e.g., a proximity sensor) to determine that an imaging device 102 has been connected to the image analysis system 108. In some embodiments, the image analysis system 108 may be connected to (via a wired or a wireless connection) a plurality of imaging devices.

The image analysis system 108 may include various components for providing the features described herein. In some embodiments, the image analysis system 108 may include one or more image analysis modules to perform the image analysis of the image data received from the imaging device 102. The image analysis modules may perform one or more imaging algorithms using the image data.

The image analysis system 108 may be connected to one or more display device 110. The image analysis system 108 may be connected (via a wireless or wired connection) to the display device 110 to provide a recommendation for a set of image data. The image analysis system 108 may transmit the recommendation to the display device 110 via the network 112. In some embodiments, the image analysis system 108 and the user computing device 110 may be configured for connection such that the user computing device 110 can engage and disengage with image analysis system 108 in order to receive the recommendation. For example, the display device 110 may engage with the image analysis system 108 upon determining that the image analysis system 108 has generated a recommendation for the display device 110. Further, a particular display device 110 may connect to the image analysis system 108 based on the image analysis system 108 performing image analysis on image data that corresponds to the particular user computing device 110. For example, a user may be associated with a plurality of histological samples. Upon determining, that a particular histological sample is associated with a particular user and a corresponding display device 110, the image analysis system 108 can transmit a recommendation for the histological sample to the display device 110. In some embodiments, the display device 110 may dock with the image analysis system 108 in order to receive the recommendation.

In some implementations, the imaging device 102, the image analysis system 108, and/or the display device 110 may be in wireless communication. For example, the imaging device 102, the image analysis system 108, and/or the display device 110 may communicate over a network 112. The network 112 may include any viable communication technology, such as wired and/or wireless modalities and/or technologies. The network may include any combination of Personal Area Networks ("PANs"), Local Area Networks ("LANs"), Campus Area Networks ("CANs"), Metropolitan Area Networks ("MANs"), extranets, intranets, the Internet, short-range wireless communication networks (e.g., ZigBee, Bluetooth, etc.), Wide Area Networks ("WANs")—both centralized and/or distributed—and/or any combination, permutation, and/or aggregation thereof. The network 112 may include, and/or may or may not have access to and/or from, the internet. The imaging device 102 and the image analysis system 108 may communicate image data. For example, the imaging device 102 may communicate image data associated with a histological sample to the image analysis system 108 via the network 112 for analysis. The image analysis system 108 and the display device 110 may communicate a recommendation corresponding to the image data. For example, the image analysis system 108 may communicate a diagnosis regarding whether the image data is indicative of a disease present in the tissue sample. In some embodiments, the imaging device 102 and the image analysis system 108 may communicate via a first network and the image analysis system 108 and the display device 110 may communicate via a second network. In other embodiments, the imaging device 102, the image analysis system 108, and the display device 110 may communicate over the same network.

One or more third-party computer systems 115 ("computer system 115") may communicate with the imaging device 102, the image analysis system 108, and/or the display device 110. In some embodiments, the computer system 115 may communicate directly with the imaging device 102, the image analysis system 108, and/or the display device 110 directly or via the network 112.

The computer system 115 can provide information to change functionality on the imaging device 102, the image analysis system 108, and/or the display device 110, or even the network 112. For example, the information may be new software, a software update, new or revised lookup tables, or data or any other type of information that is used in any way to generate, manipulate, transfer or render an image (all being referred to herein as an "update" for ease of reference). The update may be related to, for example, image compression, image transfer, image storage, image display, image rendering, etc. The computer system 115 may provide a message to the device or system to be updated or may provide a message to a user who interacts with the system control updating the system. In some embodiments, the computer system 115 provides an update automatically, e.g., periodically or as needed/available. In some embodiments, the computer system 105 may provide an update in response to receiving an indication from a user provide the update (e.g., affirmation for the update or a request for the update).

With reference to an illustrative embodiment, at [A], the imaging device 102 can obtain a tissue sample (or "tissue block"). In an example, the tissue sample may be biological tissue that has been removed from a person or an animal for analysis. The tissue sample may be a histological sample. The tissue sample may be sectioned (sliced) to generate one or more sections of the tissue sample. The imaging device 102 can image (e.g., scan, capture, record, etc.) the one or more sections of the tissue sample. As will be discussed in further below, in order to prepare portions (e.g., slices or "sections") of the tissue sample for analysis, various histological techniques may be performed. The imaging device 102 can capture an image of a stained section from the tissue sample and store corresponding block and serial tissue section data in the imaging device 102. The imaging device 102 may obtain the data based on a user interaction. For example, a user may provide an input through a user interface (e.g., a graphical user interface ("GUI")) and request that the imaging device 102 image the tissue sample. Further, the user can interact with imaging device 102 to cause the imaging device 102 to image sections from the tissue sample. For example, the user can toggle a switch of the imaging device 102, push a button of the imaging device 102, provide a voice command to the imaging device 102, or otherwise interact with the imaging device 102 to cause the imaging device 102 to image the sections from the tissue sample. In some embodiments, the imaging device 102 may image sections from the tissue sample based on detecting, by the imaging device 102, that a glass slide holding a stained tissue section has been placed in a viewport of the imaging device 102. For example, the imaging device 102 may determine that a glass slide holding a stained tissue section has been placed on a viewport of the imaging device 102 and, based on this determination, image the tissue section.

The imaging device 102 can obtain images of sections of the tissue sample data. Various histological techniques may be performed on the section. The imaging device 102 can capture an image of each section, and store the images for subsequent analysis. The imaging device 102 may obtain the section images based on a user interaction. For example, a user may provide an input through a user interface and request that the imaging device 102 image the section. Further, the user can interact with imaging device 102 to cause the imaging device 102 to image the section.

The imaging device 102 can transmit a signal 6 to the image analysis system 108 representing the captured image data (e.g., the block data and the slice data). The imaging device 102 can send the captured image data as an electronic signal 6 to the network 112, which provides the image data as a signal 8 to the image analysis system 108. The signal may include and/or correspond to a pixel representation of the section data. It will be understood that the signal can include and/or correspond to more, less, or different image data. For example, the signal may correspond to multiple sections, and may represent a first section data and a second section data. Further, the signal may enable the image analysis system 108 to reconstruct the tissue sample using the section data.

The image analysis system 108 can perform image analysis on the block data and the slice data provided by the imaging device 102. In order to perform the image analysis, the image analysis system 108 may utilize one or more image analysis modules that can perform one or more image processing functions. Each image analysis model can include computer executable instructions which are run by one or more computer hardware processors to perform certain functionality. In an example, an image analysis module may include an imaging algorithm, a machine learning model, a convolutional neural network, or any other modules for performing the image processing functions. In another example, an image analysis module can include one or more spatial analysis algorithms to measure the proximity between markers within an image of a section, or across images of sections of the tissue sample. In some examples, based on performing the image processing functions, the image analysis module can determine a likelihood that the block data and the slice data correspond to the same tissue block. For example, an image processing function may include an edge analysis of the block data and the slice data and based on the edge analysis, determine whether the block data and the slice data correspond to the same tissue block. The image analysis system 108 can obtain a confidence threshold from the display device 110, the imaging device 102, or any other device. In some embodiments, the image analysis system 108 can determine the confidence threshold based on a response by the display device 110 to a particular recommendation. Further, the confidence threshold may be specific to a user, a group of users, a type of tissue block, a location of the tissue block, or any other factor. The image analysis system 108 can compare the determined confidence threshold with the image analysis performed by the image analysis module. Based on this comparison, the image analysis system 108 can generate a recommendation indicating a recommended action for the display device 110 based on the likelihood that the block data and the slice data correspond to the same tissue block. In other embodiments, the image analysis system 108 can provide a diagnosis regarding whether the image data is indicative of a disease present in the tissue sample, for example, based on the results of a machine learning algorithm.

The image analysis system 108 can provide information to the display device 110. In an example, the image analysis system 108 can send the information as a signal 6 to the network 112 which provides the information as a signal 8 to the display device 110. The signal may include results of the image analysis, for example, feature information or semantic segmentation information. The display device 110 can assist the pathologist in determining the diagnosis. In some embodiments, the image analysis system 108 may transmit a series of recommendations corresponding to a group of tissues blocks and/or a group of slices. The image analysis system 108 can include, in the recommendation, a recommended action of a user. For example, the recommendation may include a recommendation for the user to review the tissue block and the slice(s). Further, the recommendation may include a recommendation that the user does not need to review the tissue block and the slice(s).

Figure 2:
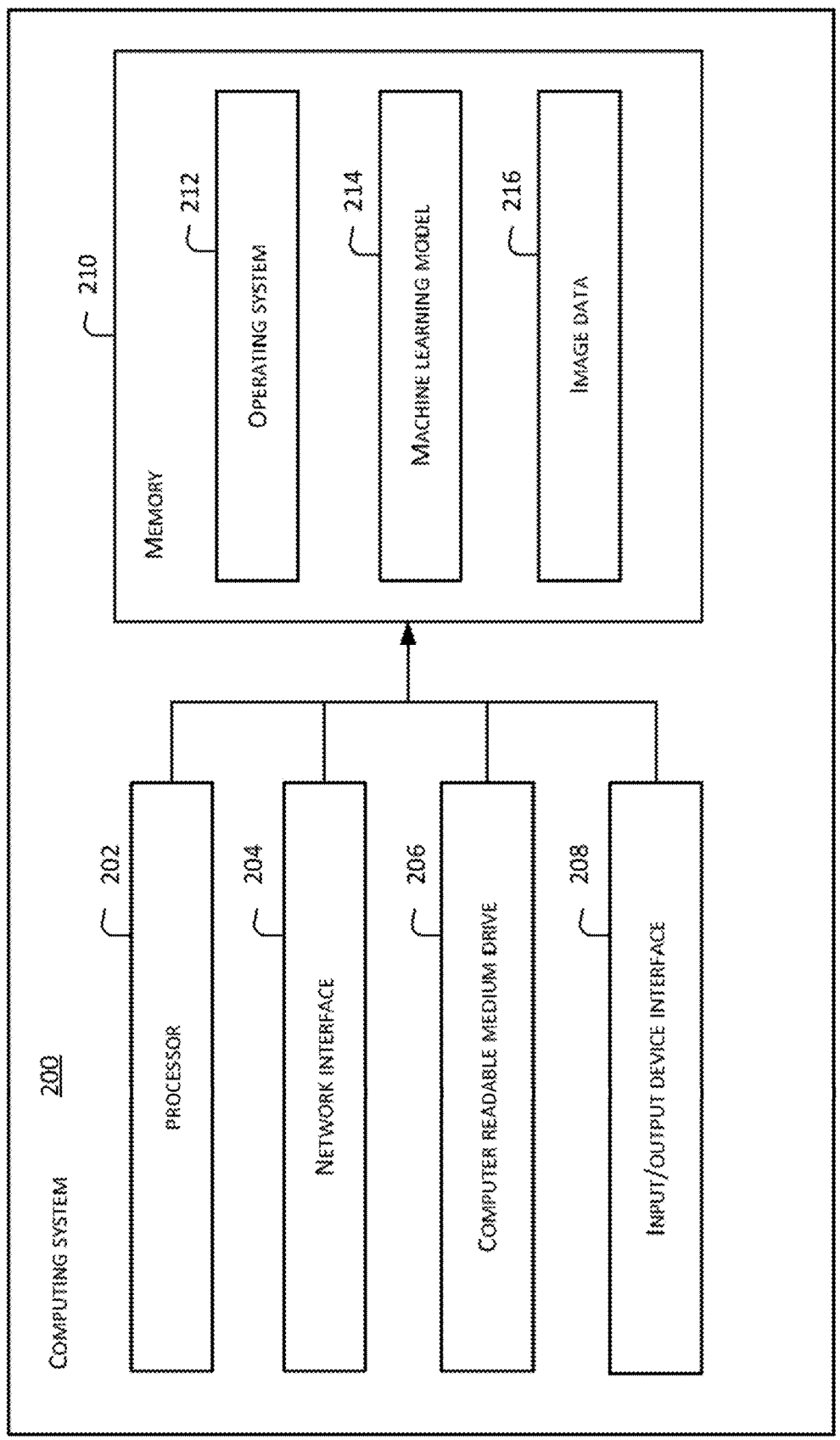
FIG. 2 is an example computing system which can implement all or portions of embodiments of the imaging device, image analysis system, and user computing device of the imaging system illustrated in FIG. 1.

FIG. 2 is an example computing system 200 which, in various embodiments, can implement the functionality of the imaging device 102, image analysis system 108, and/or the display device 110 of the system illustrated in FIG. 1. Referring to FIG. 2, the computing system 200 may include one or more hardware processors 202, such as physical central processing units ("CPUs"), one or more network interfaces 204, such as a network interface cards ("NICs"), and one or more computer readable medium 206. The computer readable medium can be, for example, a high-density disk ("HDDs"), solid state drives ("SDDs"), flash drives, and/or other persistent non-transitory computer-readable media. The computing system 200 may also include an input/output device interface 208, such as an input/output ("IO") interface in communication with one or more microphones, and one or more non-transitory computer readable memory (or "medium") 210, such as random-access memory ("RAM") and/or other volatile non-transitory computer-readable media.

The network interface 204 can provide connectivity to one or more networks or computing systems. The hardware processor 202 can receive information and instructions from other computing systems or services via the network interface 204. The network interface 204 can also store data directly to the computer-readable memory 210. The hardware processor 202 can communicate to and from the computer-readable memory 210, execute instructions and process data in the computer readable memory 210, etc.

The computer readable memory 210 may include computer program instructions that the hardware processor 202 executes in order to implement one or more embodiments. The computer readable memory 210 can store an operating system 212 that provides computer program instructions for use by the computer processor 202 in the general administration and operation of the computing system 200. The computer readable memory 210 can further include program instructions and other information for implementing aspects of the present disclosure. In one example, the computer readable medium includes instructions for determining semantic segmentation using a set of images depicting at least a portion of a WSI of a stained tissue sample. The non-transitory computer storage medium configured to store image data 216 comprising images derived from the WSI, including a first image of a tissue sample at a first resolution, a second image of the tissue sample at a second resolution that is higher than the first resolution, and a third image of the tissue sample at a third resolution that is higher than the second resolution, the first, second, and third images depicting at least a portion of a same area of the tissue sample. The executable instructions, when executed by the one or more hardware processors 202, configure the one or more hardware processors to use a machine learning model 214 to generate first feature information based on the first image, generate second feature information based on the second image and at least a portion of the first feature information, and generate third feature information based on the third image and at least a portion of the second information. The executable instructions, when executed by the one or more hardware processors 202, further configure the one or more hardware processors to determine segmentation information relating to the WSI based on the third feature information. The executable instructions, when executed by the one or more hardware processors, can further configure the one or more hardware processors to generate the first feature information using a first encoder-decoder process trained for semantic segmentation, wherein the first feature information is an intermediary output of the first encoder-decoder semantic segmentation process, generate the second feature information using a second encoder-decoder process trained for semantic segmentation, wherein the second feature information is an intermediary output of the second encoder-decoder semantic segmentation process, and generate the third feature information using a third encoder-decoder process trained for semantic segmentation, wherein the first feature information is output of the third encoder-decoder semantic segmentation process. In another example, the computer readable medium 210 includes instructions to execute one or more of the processes 1400 (FIG. 14) and/or 1500 (FIG. 15). In some embodiments, multiple computing systems 200 may communicate with each other via respective network interfaces 204, may implement multiple sessions each session with a corresponding connection parameter (e.g., each computing system 200 may execute one or more separate instances of processes described herein).

Figure 3:
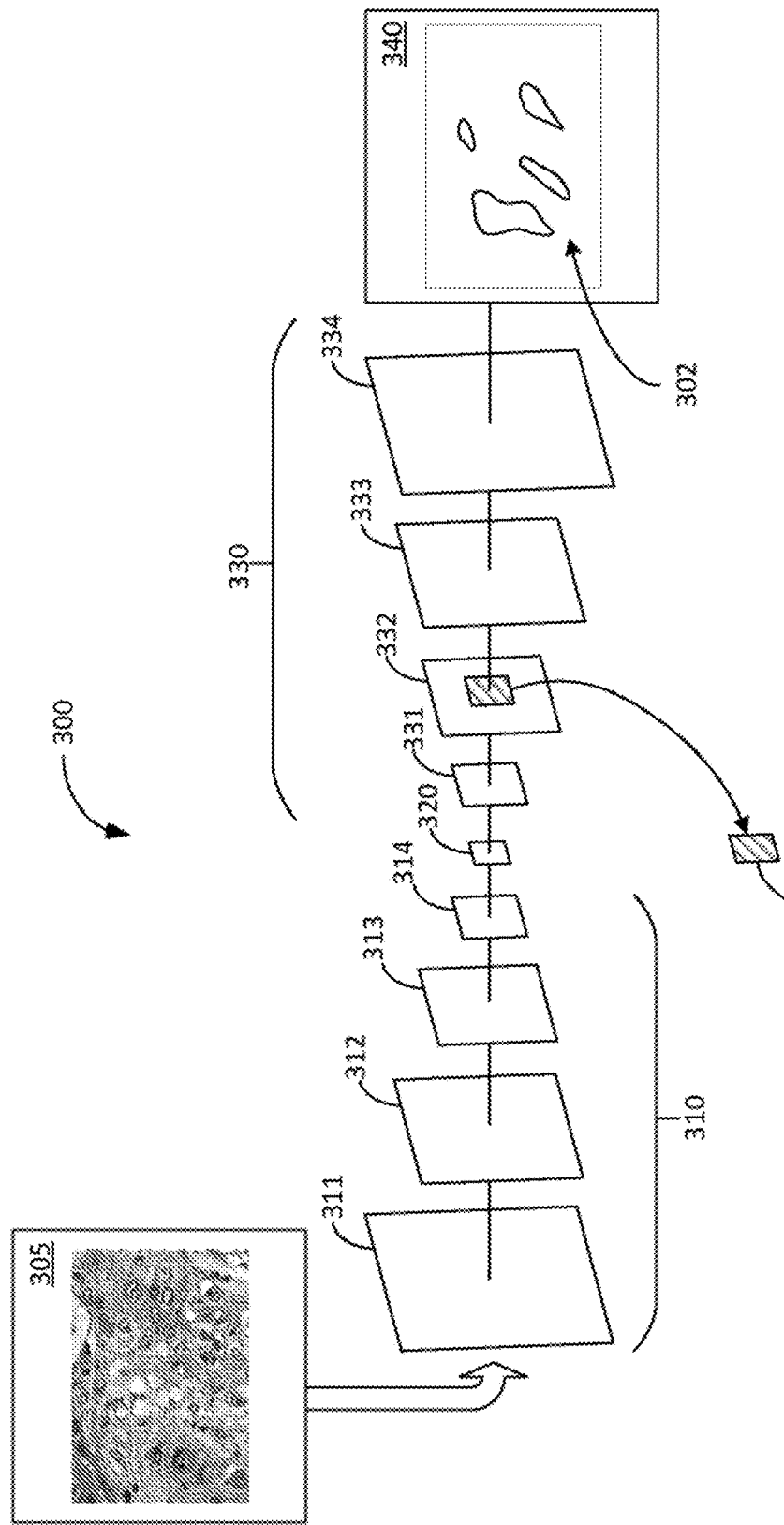
FIG. 3 illustrates an example an embodiment of an encoder-decoder system ("encoder-decoder") for determining semantic segmentation of features in pathology images, the encoder-decoder providing an intermediary output of feature information, according to some embodiments.

FIG. 3 illustrates an example an embodiment of an exemplary encoder-decoder system ("encoder-decoder") 300 that can be one of multiple encoder-decoders in an image analysis system architecture for classifying structures and features in pathology images. Each encoder-decoder is structured with multiple layers and trained for processing images of a certain resolution to determine feature information and/or classify pixels in the image. In some embodiments, the encoder-decoder includes a convolutional neural network. Images in a set of MR Images that are the highest resolution may be referred to as "target images." Images in a set of MR Images that are not the highest resolution may be referred to as "context images." The encoder-decoders that process images that are context images are configured to provide feature information to an encoder-decoder that is processing a higher resolution image. The feature information can be determined during the encoder-decoder process where the feature information can be intermediary information that is not the result of the processing by an entire encoder-decoder process (e.g., an output that results from processing an image through all of the layers of the encoder and the decoder).

The exemplary encoder-decoder 300 includes an encoder 310 and a decoder 330. The encoder 310 includes multiple layers, for example, encoder layers 311, 312, 313, and 314. The decoder 330 includes multiple layers, for example, decoder layers 331, 332, 333, and 334. In various embodiments, the encoder-decoder 300 may include a different number of encoder and decoder layers. The encoder 310 receives an input image 305, for example, a context image of a set of MR Images. The encoder 310 processes the images to determine feature information relating to features, structures, and/or objects in the image 305. The feature information may include structural classification information that can be used by the decoder 330 to determine a class 302 for each pixel in output information (or an output image) 340, which can be, for example, sematic segmentation of each pixel that is representative of the features, structures and objects in the image 305. The encoder 310 produces output information 320 that is provided to the decoder 330 as an input. The decoder 330 processes the information 320 and produces the output image 340. In this example, the output image 340 is considered a "final output" of the encoder-decoder 300.

The encoder-decoder 300 also can generate feature information 351. The encoder-decoder 300 can provide the feature information 351 as an output 345, and the feature information 351 can be used as an input for another encoder-decode, for example, an encoder-decoder that is processing images of a higher resolution in the set of MR Images. The feature information 351 is an intermediary output from the encoder-decoder 300. In various embodiments, the feature information 351 can be based on information generated by any of the layers of the encoder-decoder 300. In some embodiments, the feature information 351 corresponds to a resolution of a layer of an encoder-decoder that receives the feature information.

FIGS. 4A and 4B illustrate examples of sets of MR Images that can be used as input to one or more encoder-decoders. FIG. 4A illustrates a set of concentric images 400. In FIG. 4A, a set of concentric images 400 is illustrated as various sizes representing a portion (or area) of a WSI that the image depicts. In some examples, the actual X, Y pixel dimensions of the images 400 is the same (or approximately the same). Image 402 is the highest resolution image (a target image) and depicts the smallest area of the WSI. Images 404, 406, 408, and 410 are context images, each having progressively looser resolutions and depicting the same (or nearly the same) area of the WSI. As described further in reference to FIG. 7, feature information generated by an encoder-decoder based on a context image 404, 406, 408, 410 can be provided to an encoder-decoder processing a context image of a higher resolution or an encoder-decoder processing the target image 402.

FIG. 4B illustrates a set of images 450. In this example, the set of images 450 includes images of five different (and increasing) resolutions, arranged in image layers 452, 454, 456, 458, and 460, respectively. Images in image layers 452, 454, 456, and 458 are context images. Images in image layer 460 are target images, have the highest resolution, and depict the smallest area of the WSI. In this example, each layer is illustrated as being a different size, however, collectively the images in each layer represent (or depict) the same area of the WSI. As described further in reference to FIG. 7, feature information generated by an encoder-decoder based on a context image in image layers 452, 454, 456, 458 can be provided to an encoder-decoder processing a context image of a higher resolution or an encoder-decoder processing a target image in image layer 460.

FIG. 5 illustrates another example of a set of MR Images that can be used as input to one or more encoder-decoders configured for semantic segmentation of a WSI 512 (or another high-resolution image). In this arrangement, the WSI 512 includes six image portions labeled A. The set of MR images includes a rectangular highest context lowest resolution image 510 which includes four image portions labeled B, and progressively lower context and higher resolution image 508 (which includes four image portions labeled C), image 506 (which includes four image portions labeled D), image 504 ((which includes four image portions labeled E), and image 502 which depicts a portion of the WSI depicted by image 504. Images 510, 508, 506, and 504 are context images, image 502 is a target image. As described further in reference to FIG. 7, feature information generated by an encoder-decoder based on a context image 510, 508, 506, and 504 can be provided to an encoder-decoder processing a context image of a higher resolution or an encoder-decoder processing a target image, for example image 502.

Figure 6:
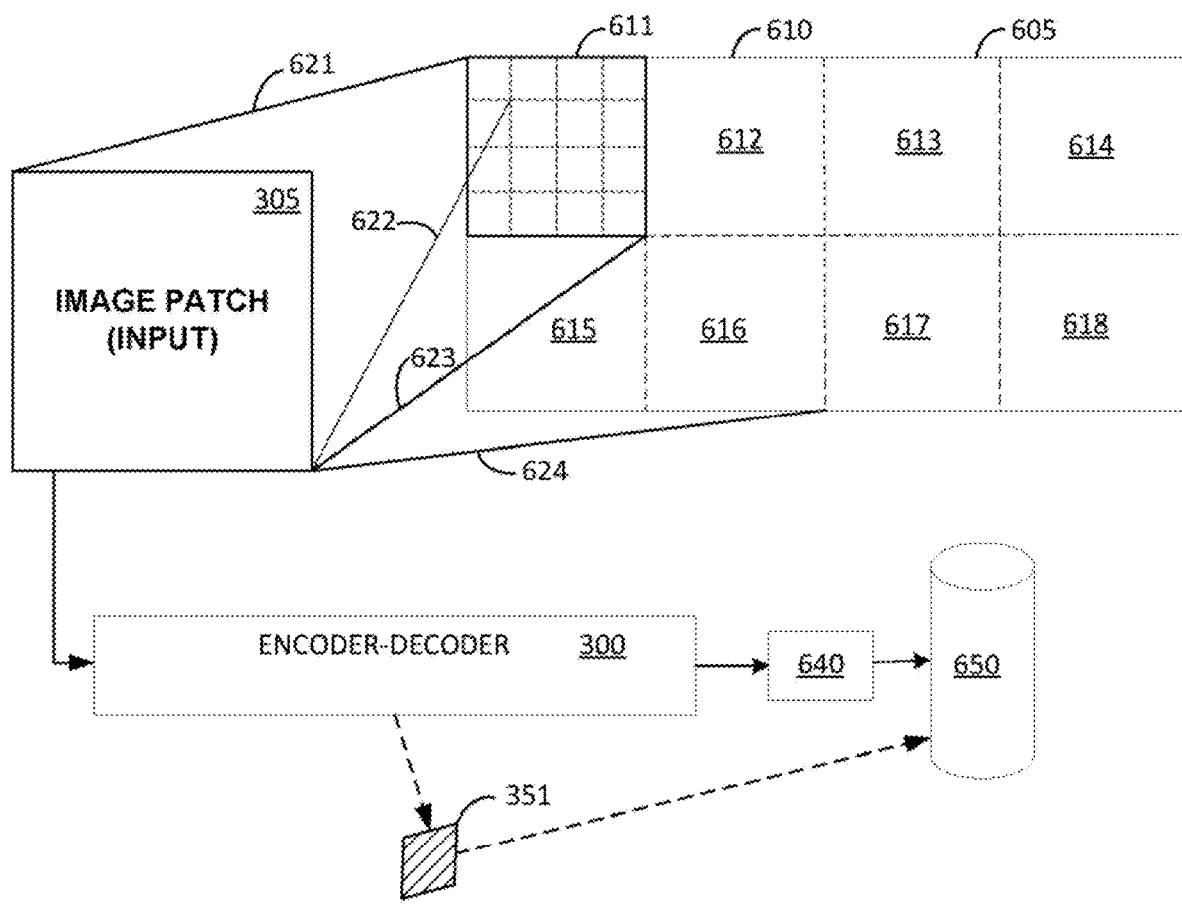
FIG. 6 illustrates an example of an encoder-decoder that is trained to determine feature information of certain resolution of a multi-resolution image.

FIG. 6 illustrates an example of an embodiment of encoder-decoder 300 that is trained to determine feature information of a certain resolution of a multi-resolution image. In the example of FIG. 6, WSI 605 includes images 611, 612, 613, 614, 615, 616, 617, 618. Images 611, 612, 615, and 616 are part of a high context low resolution image 610. Image 611 includes a number of target images depicted by the dashed lines. The encoder-decoder 300 includes an encoder portion and a decoder portion, and can include a convolutional neural network. The encoder-decoder 300 can includes multiple layers (e.g., similar to the encoder-decoder 310/330 illustrated in FIG. 3). The encoder-decoder 300 can be one of the encoder-decoders illustrated in the encoder-decoder architecture 700 of FIG. 7, which are each configured to process images of a certain resolution, and each branch being configured to process images of a different resolution than the other branches. In operation, the encoder-decoder 300 receives an image 305 and determines a classification of structures in the image 305, and produces pixel classification information 640 representative of the image 305. The pixel classification information can be stored in a non-transitory storage component 650 (e.g., a database). The pixel classification information can include semantic segmentation. The pixel classification information can include an assigned class to one or more pixels of image 305, or each pixel of image 305. In the process of generating pixel classification information 640, the encoder-decoder 300 generates feature information 351. the feature information 351 can be saved in a non-transitory storage component 650 (e.g., a database). In the encoder-decoder architecture 700 illustrated in FIG. 7, the feature information 351 can be accessed by an encoder-decoder processing higher resolution images and used as an input to produce more accurate pixel classification information.

The input image 305 depicts at least a portion of the WSI. For example, the input image 305 is an image derived from the WSI 605, for example, image 610, 611 or a target image that depicts a portion of image 611, or an image of another resolution that depicts a portion of the WSI. In some embodiments, whether the input image 305 is a target image (depicted by lines 621, 622), a context image 611 (depicted by lines 621 and 623), context image 610 (depicted by lines 621 and 624), another context image having a different resolution greater than the resolution of the target image, (for example, a quarter portion of image 611) the input image 305 has the same pixel X, Y dimensions (i.e., regardless of the context or target image it is based on, and correspondingly varies in resolution).

Figure 7:
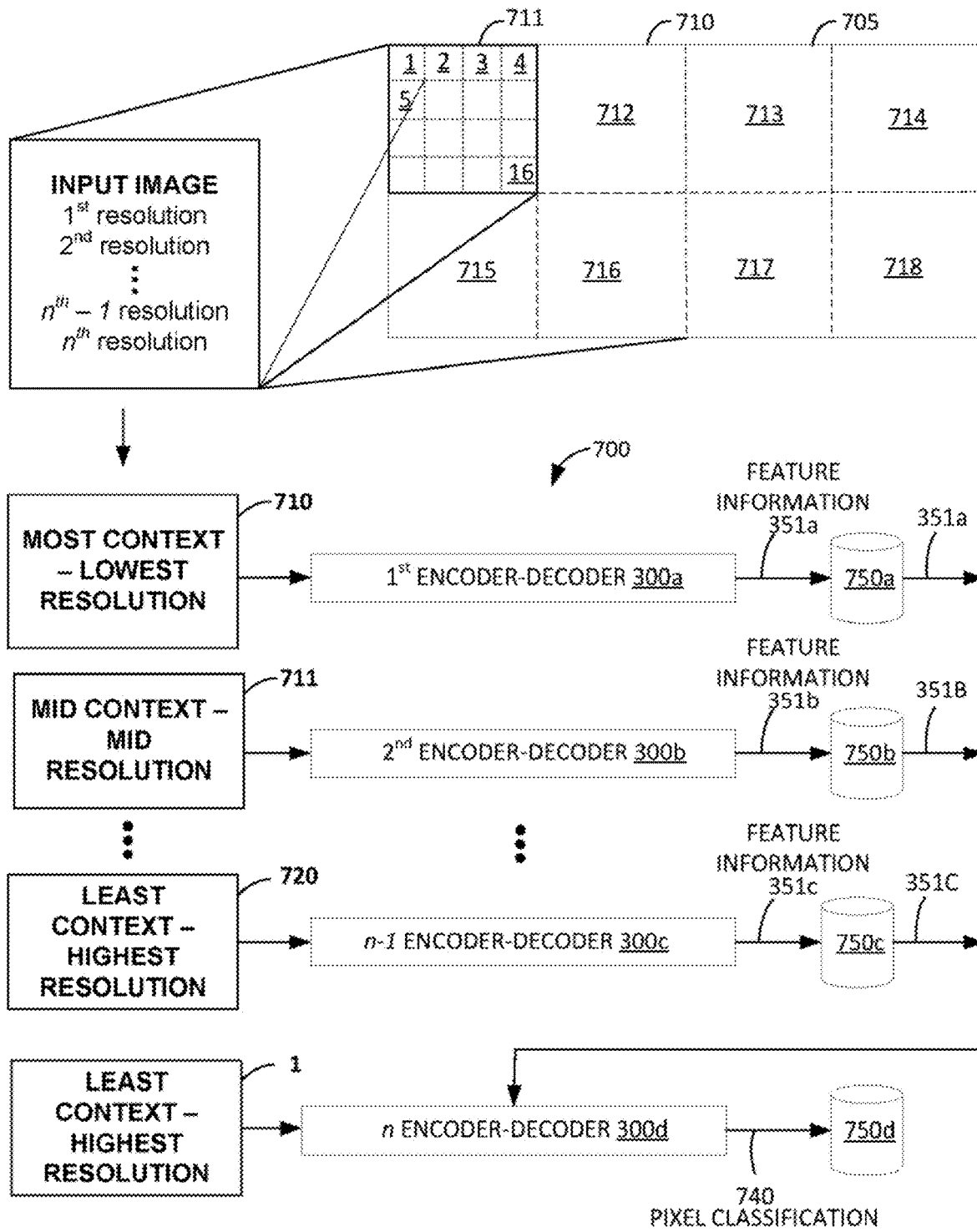
FIG. 7 illustrates an example of a set of encoder-decoders that are each trained to determine feature information of a certain resolution of a multi-resolution image, where certain encoder-decoders may be configured to provide feature information to at least one other encoder-decoder, and certain encoder-decoders may be configured to receive feature information from another encoder-decoder.

FIG. 7 illustrates an example of an embodiment of an encoder-decoder architecture (or system) 700 that includes multiple encoder decoders (each of which may be an encoder-decoder 300 as illustrated in FIG. 3), each trained to process images to determine feature information and/or pixel classification information of a certain resolution of a multi-resolution set of images. The embodiment shown in FIG. 7 illustrates an example of "inference" functionality. That is, when the encoder-decoders have been trained and are processing images for non-training purposes (e.g., production). This is sometimes referred to as processing images for "inference" (or "inferencing") instead of for training. That is, when unknown/new images (that have not been annotated) are processed for determining information about features, structures, objects, etc. in the images and/or classification of the features, structures and objects. In this example, the encoder-decoders 300a-c that process context images may not produce pixel classification information (i.e., generally thought of as being the decoder portion) but instead produce feature information 351 as an output of the encoder portion. Accordingly, not all (or none) of the decoder portion is used for the context images processing encoder-decoders 300a-c. The encoder decoder 300d processes the highest resolution target images using its trained encoder-decoder functionality, and also uses feature information 351 produced by the context processing encoder-decoders 300a-c as an input, as described herein. In an example, encoder-decoder architecture 700 includes multiple encoder-decoders, each one structured and trained to process images of a certain resolution.

This example of a WSI 705 includes images 711, 712, 713, 714, 715, 716, 717, 718 of a certain resolution. Image 710 represents a high context low resolution image of the WSI 705. Images 711, 712, 715, 716 each depict a portion of image 710 and are of a higher resolution than image 710. Images 1-16 depict a portion of image 711 and are of a higher resolution than image 711. In this example, high context, low resolution image 710, mid-context mid-resolution images 711, 712, 715, 716, and target images 1-16 can be arranged as a set of MR Images. As illustrated in FIG. 7, the encoder-decoder architecture 700 includes multiple encoder-decoders. The multiple encoder-decoders are represented by a first encoder decoder 300a, a second encoder-decoder 300b, an n (or n$^{th}$) encoder-decoder 300d, and a n-1 encoder-decoder 300c. n-1 encoder-decoder 300c represents one or more encoder-decoders that are configured to process images that have resolutions less than the target images (the highest resolution images processed by encoder-decoder 300d) and greater than the context images processed by the $2^{nd}$ encoder-decoder 300b. In some embodiments of the encoder-decoder architecture 700, there are only three branches (and accordingly a fourth branch that includes the illustrated n−1 encoder-decoder 300c is not included in the encoder-decoder architecture 700. In some embodiments of the encoder-decoder architecture 700, there are more than four branches and the n−1 encoder-decoder 300c represents the fourth branch and any additional intermediary branches.

In this example, first encoder-decoder 300a is structured and trained to process the most context, lowest resolution images of the WSI 705 (for example image 710 having a first resolution) and produce feature information 351a that can be output and stored in a non-transitory computer storage medium information 750a. Second encoder-decoder 300b is structured and trained to process the mid-context mid-resolution images of the WSI 705 (for example, image 711 having a second resolution, that is greater than the resolution of image 710) and produce feature information 351a that can be output and stored in a non-transitory computer storage medium information 750a.

The n−1 encoder-decoder 300c is structured and trained to process other mid-context mid-resolution images of the WSI 705 and produce feature information 351c that can be output and stored in a non-transitory computer storage medium information 750c. As indicated above, n−1 encoder-decoder 300c represents one or more intermediate encoder-decoders that process images having a resolution between the second resolution and the resolution of the target images, represented by image 720. Accordingly, in various implementations, n−1 encoder-decoder 300c represents 0 additional branches, or 1, 2, 3, 4, 5, 6, 7, 8 9, or 10 additional branches, or more than 10 additional branches. As an example, the set of images illustrated in FIGS. 4A and 4B include images having five different resolutions (e.g., having five image layers, each having a different resolution). For processing these sets of images, the encoder decoder architecture 700 can include five branches, and in that case the n−1 encoder-decoder 300c represents two branches.

The n encoder-decoder 300d is structured and trained to process target images (the lowest context highest resolution images) of the WSI 705 (for example, image 1), and to use the previously generated feature information 351a-c to produce pixel classification information 740 that can be output and stored in a non-transitory computer storage medium information 750c. The pixel presentation information 740 can include, for example, one or more of class labels for each of the pixels or groups of pixels in the input target image, semantic segmentation information, vector information indicative of the classification pixels or features, structures or objects depicted in the target image processed.

When these encoder-decoders are being trained, they process an input image and can produce an output of pixel classification information for features depicted in the input image. When the encoder-decoders have been trained and are being used for "inferencing" or "production," the encoder-decoders 300a, 300b, 300c that are used to process context images (i.e., images other than the highest resolution target images) are configured to produce a feature information output 351a, 351b, 351c that can be stored in a non-transitory computer storage medium 750a, 750b, 750c. The encoder decoder 300d that is used to process the target image, is configured to receive, or access, the feature information 351a, 351b, 351c generated by the encoder-decoders processing the context images, and use the feature information 351a, 351b, 351c along with a target image to generate pixel classification information 740, which can be stored on a non-transitory computer storage medium 750d. In the example illustrated in FIG. 7, each encoder-decoder other than $n^{th}$ encoder-decoder may be configured to provide its feature information to each higher resolution/lower context encoder-decoder, resulting in each encoder-decoder other than the first encoder-decoder incorporating the context of the lower resolution encoders in its processing, with the $n^{th}$ encoder-decoder incorporating the context of each of the other encoder-decoders.

Figure 8:
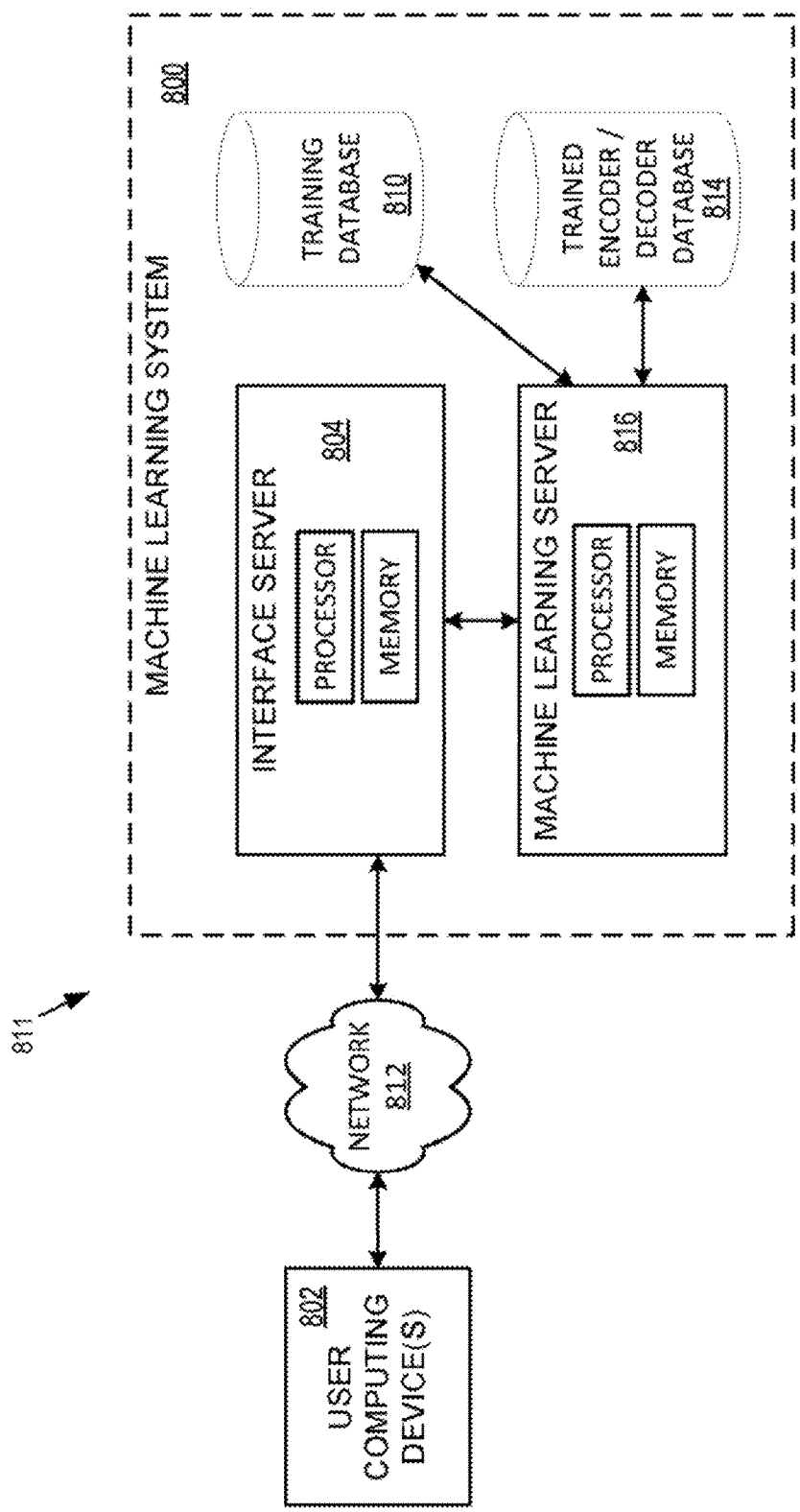
FIG. 8 illustrates an exemplary training and/or inference platform of a machine learning system.

In some embodiments, encoder-decoders described herein can be convolutional neural networks trained to generate feature information including classification information (e.g., semantic segmentation). The convolutional neural networks can be trained using sets of annotated tissue sample images. FIG. 8 illustrates an exemplary training and/or inference platform of a machine learning system in which the machine learning system 800 may train and/or use machine learning models implemented in encoder-decoders, for example, the encoder-decoders 300a, 300b, 300c, 300d illustrated in FIG. 7. The environment 811 may include one or more user computing devices 802 ("user computing device 802") and a network 812. The machine learning system 800 may include an interface server 804, a machine learning server 816, a training database 810, and a trained model database 814. In an example, the training database 810 is used to store data sets that are used for training. These data sets may include training images, and annotations associated with the training images. The trained encoder-decoder database 814 can include weights for the neural networks in one or more branches of an encoder-decoder architecture, the weights generated during training of neural networks in the encoder decoders. After weights are generated for one or more branches, they may be communicated to other encoder-decoder systems which are processing images similar to the images used to generate the weights. Each of the interface server 804 and the machine learning server 816 may include at least a processor and a memory. Each of the interface server 804 and the machine learning server 816 may include additional hardware components, such as the hardware component(s) describe above with respect to FIG. 2.

In various embodiments, the environment 811 may be used to train one or more machine learning models. For example, the user computing device 802 may transmit (via the network 812) image data, which can include annotated image data, to the interface server 804 for training purposes. The interface server 804 may communicate with the machine learning server 816, such as by transmitting the image data. The machine learning server 816 may store the image data and other training data, such as class label masks, in the training database 810. The machine learning server 816 may train one or more machine learning models using the image data, which can include the annotated image data. Exemplary annotated image data may include labelled image data that are based on an annotated image(s) from a pathologist. The trained machine learning models may be configured to classify input image data. In other words, the trained machine learning models may be configured to output a predicted classification for new input data, such as by predicting whether a patch in the image corresponds to a class, such as, whether abnormal cells are present or not, and if there are abnormal cells, a type of cancer cells. The machine learning server 816 may store the machine learning model(s) in the trained model database 814.

In various embodiments, the exemplary environment 811 may be used to apply one or more trained machine learning models. For example, the user computing device 802 may transmit, via the network 812, image data to the interface server 804 for classification purposes. The interface server 804 may communicate with the machine learning server 816, such as by transmitting the image data to be classified. The machine learning server 816 may retrieve a trained machine learning model from the trained model database 814. The machine learning server 816 apply one or more machine learning models to the input image data to receive a predicted classification. The interface server 804 can receive the predicted classification and may transmit, via the network 812, the predicted classification to the user computing device 802. In various embodiments, the interface server 804 can present a user interface, which includes the predicted classification, to the user computing device 802.

In various embodiments, the machine learning system 800 or components thereof are implemented by one or more virtual machines implemented in a hosted computing environment. The hosted computing environment may include one or more rapidly provisioned and/or released computing resources. The computing resources may include hardware computing, networking and/or storage devices configured with specifically configured computer-executable instructions. A hosted computing environment may also be referred to as a "serverless," "cloud," or distributed computing environment.

Figure 9:
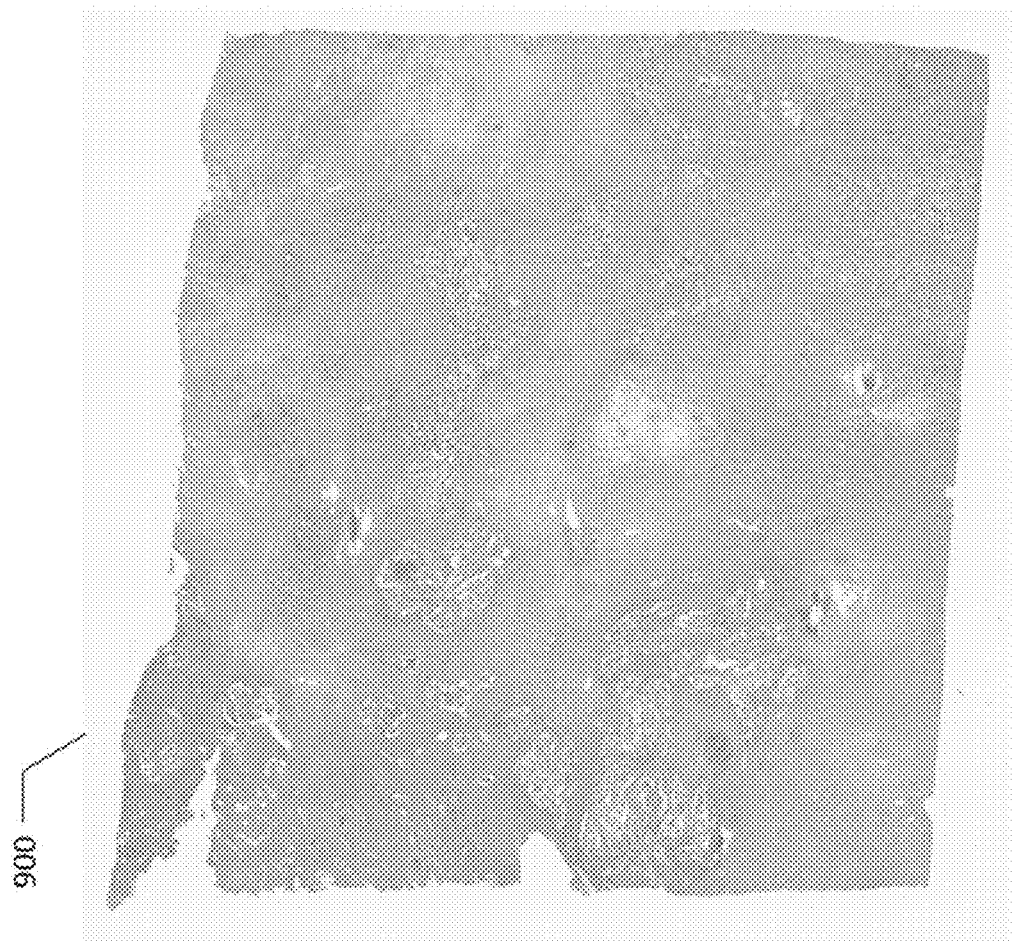
FIG. 9 illustrates an exemplary image of a scanned tissue sample.

FIG. 9 illustrates an exemplary image 900 of a scanned tissue sample. The exemplary image 900 may be a WSI. The exemplary image 900 may be a scan of a microscope slide and may be stored in a single high-resolution image file. The exemplary image 900 may be a whole-slide image from a breast biopsy. In an example, exemplary image 900 may have a full spatial resolution of 80K×80K pixels, which can be approximately 2 GB in compressed storage size at 40-times magnification. As described herein, the exemplary image 900 may be too large to be processed by a GPU or another processor all at once with certain machine learning (such as deep learning) algorithms and/or models. An exemplary GPU or another processor may not be able to fit an entire high-resolution image into memory for image classification purposes.

Figure 10:
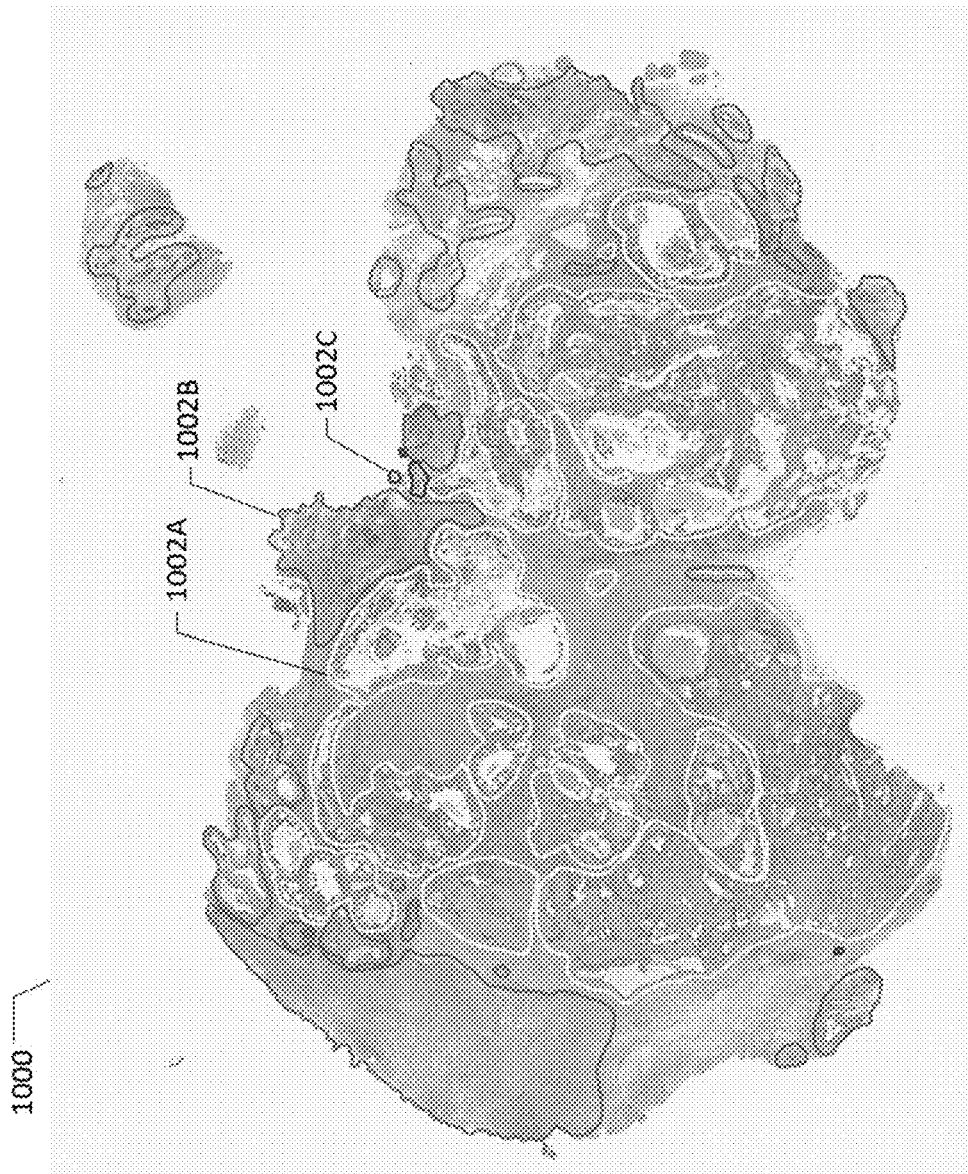
FIG. 10 illustrates an exemplary image of a scanned tissue sample with annotations by a pathologist.

FIG. 10 illustrates an exemplary image 1000 of a scanned tissue sample with annotations by one or more pathologists. The exemplary image 1000 of FIG. 10 may be similar to the exemplary image 900 of FIG. 9. However, in contrast to the image 900 of FIG. 9, the image 1000 of FIG. 10 may be further associated with the exemplary class annotations 1002A, 1002B, 1002C from a pathologist. Exemplary class annotations may indicate areas of the image that correspond to a class label as identified by a pathologist. Exemplary class labels for the annotations 1002A, 1002B, 1002C may include, but are not limited to (some of which may be specific to the breast pathology context), ductal carcinoma in situ (DCIS), benign, inconclusive, invasive carcinoma, and normal classes. The first annotation 1002A may correspond to a DCIS (non-invasive cancer) class annotation; the second annotation 1002B may correspond to a benign class annotation; and the third annotation 1002C may correspond to an inconclusive class annotation.

Figure 11:
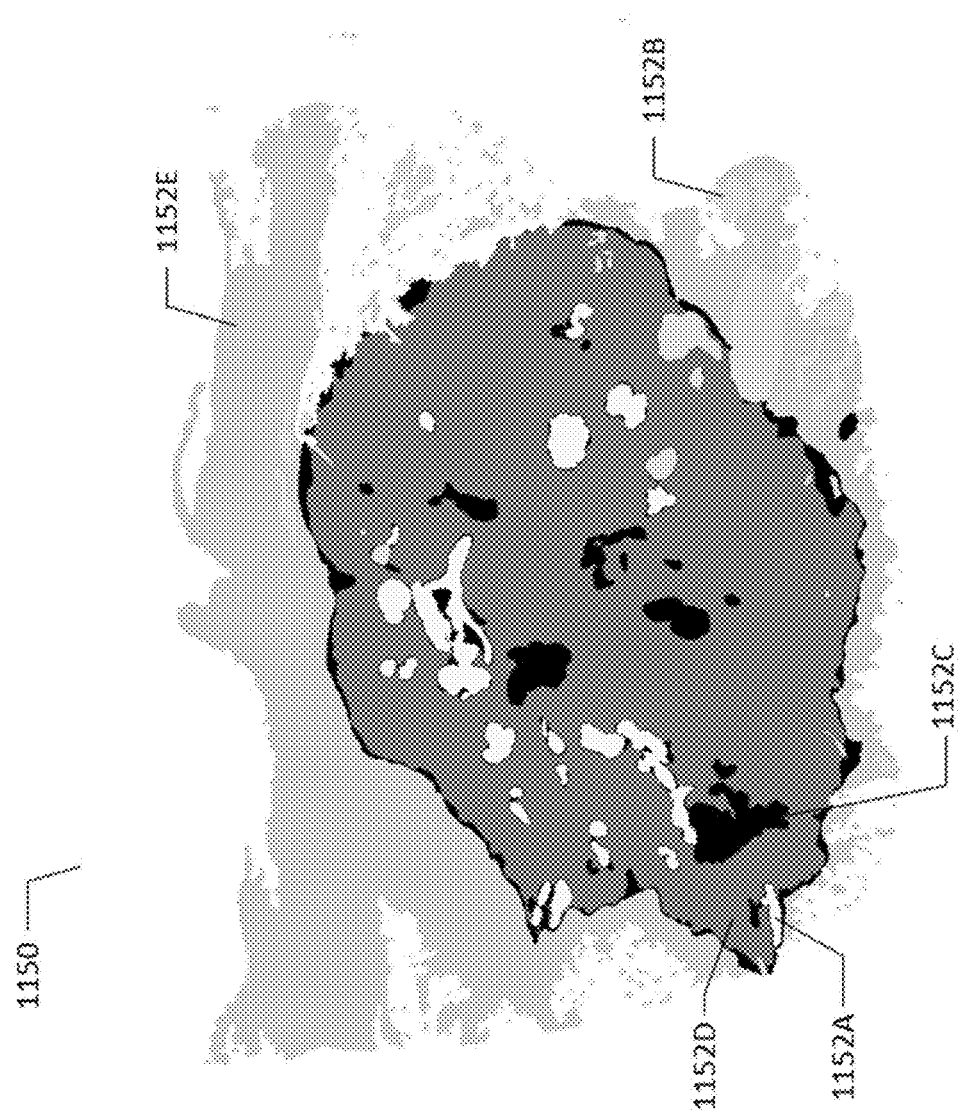
FIG. 11 illustrates an exemplary image of a scanned tissue sample with class label masks.

FIG. 11 illustrates an exemplary image 1150 of a scanned tissue sample with class label masks. The exemplary image 1150 of FIG. 11 may be similar to the exemplary image 1000 of FIG. 10. However, in contrast to the image 1000 of FIG. 10, the image 1150 of FIG. 11 may be associated with exemplary class label masks 1152A, 1152B, 1152C, 1152D, 1152E. The class label masks 1152A, 1152B, 1152C, 1152D, 1152E and their associations with the image 1150 may be generated based on an image as annotated by a pathologist (such as the image 1000 of FIG. 10 with pathologist annotations). As described herein, the image 1150 and its associations with the class label masks 1152A, 1152B, 1152C, 1152D, 1152E may be stored in the training database of a machine learning diagnostics system. Moreover, a machine learning server of the machine learning diagnostics system may use the image 1150 and its associations with the class label masks 1152A, 1152B, 1152C, 1152D, 1152E to train a machine learning model.

Exemplary class label masks may indicate areas of the image that correspond to a class label as identified by a pathologist. The first class mask 1152A may correspond to a DCIS (non-invasive cancer) class mask; the second class mask 1152B may correspond to a benign class mask; the third class mask 1152C may correspond to an inconclusive class mask due to pathologist's disagreement; the third class mask 1152C may correspond to an inconclusive class mask (where multiple pathologists are discordant, i.e., the pathologists do not agree on a class for the region); the fourth class mask 1152D may correspond to an invasive carcinoma class mask; and the fifth class mask 1152E may correspond to a normal class mask.

Figure 12:
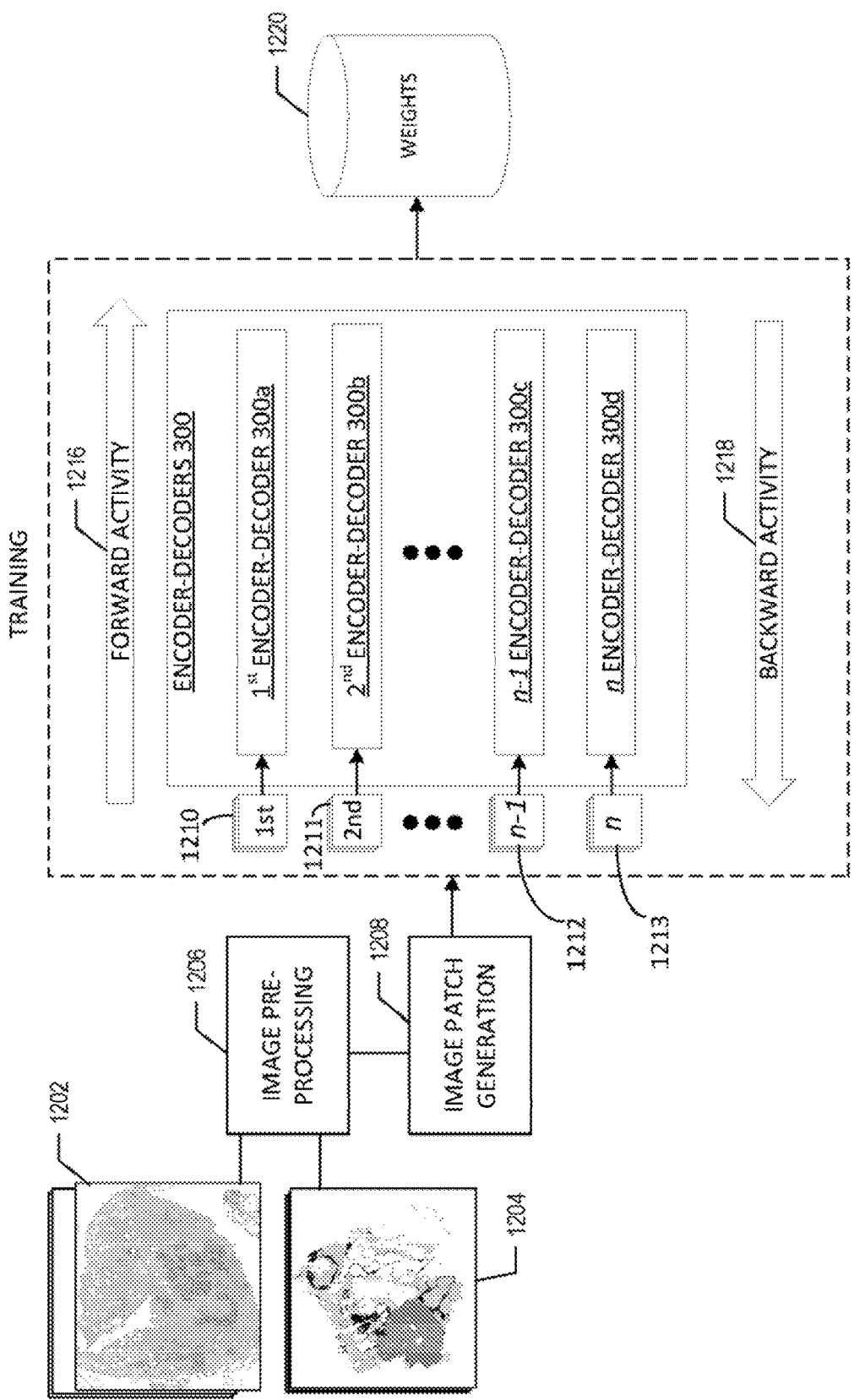
FIG. 12 is an exemplary block diagram illustrating training of an exemplary machine learning system having multiple encoder-decoders.

FIG. 12 is a block diagram illustrating training of an exemplary machine learning system having an encoder-decoder architecture 700 such as that shown in FIG. 7 that includes multiple encoder-decoders 300a-d which comprise convolutional neural networks. The four encoder-decoders 300a-d are representative of the encoder-decoders that can be included in an encoder-decoder architecture. In various examples, the encoder-decoder architecture 700 can include three or more encoder-decoders. As depicted in FIG. 12, exemplary training data may include, but is not limited to, image and labeled training data 1202, 1204. The exemplary image training data 1202 may include a set of one or more images including the exemplary image 900, which is discussed in further detail above with respect to FIG. 9. The exemplary labeled training data 1204 may include a set of one or more annotated images including the exemplary image 1150 associated with class labels, which is discussed in further detail above with respect to FIG. 11. Thus, the training data can include an enriched dataset that includes one or more images and information about features, structures, or objects in the one or more images. For example, the information in the enriched dataset may include annotations as illustrated on the image 1000 (FIG. 10) and/or pixel classification information as illustrated on the image 1150 (FIG. 11).

In some embodiments, at least some of the training data may include images where annotations are not available for those images. Some exemplary training data may instead include images where there is only a diagnosis for the entire image (such as a WSI) instead of annotations for portions of the image.

At block 1206, the machine learning server 816 (see FIG. 8) may pre-process the training data 1202, 1204. Exemplary pre-processing may include, but is not limited to, stain normalization. Exemplary stain normalization may include, but is not limited to, color normalization of stained tissue samples. Despite the standardization of staining protocols, variations in the staining results may occur due to differences in, e.g., different chemical concentrations, different conditions across slide scanners, etc. Following pre-processing of the training data 1202, 1204 by the machine learning server 816, the stains in the training data 1202, 1204 may be color normalized. Exemplary pre-processing may also include, but is not limited to, changing image characteristics, for example, one or more of brightness, contrast, dynamic range adjustment, high dynamic range (HDR) adjustment, low dynamic range (LDR) adjustment, and/or sharpness. Exemplary pre-processing may also include, but is not limited to, filtering or transformations to, for example, normalize the training images, or to introduce variations in the images for more robust training across a wider range of "different" images.

Image patch generation occurs at block 1208. In an example, the machine learning server 816 may extract patches from the processed training data. As used herein, in addition to having its ordinary meaning, the term "patch" may refer to a smaller size image from a larger size image. As described herein, a high-resolution image file may include dimensions of, for example, 80K×80K or 100K× 100K pixels. An exemplary patch size may include, but is not limited to, a smaller size patch having dimensions such as 224×224 pixels. Depending on the embodiment, patches can either be bigger or smaller than 224×224 pixels. The machine learning server 816 may extract patches from processed versions of the image and labeled training data 1202, 1204. The machine learning server 816 can extract a set of patches that may be the same dimensions but of various resolutions, based on the expected image resolutions that the encoder-decoders will be processing. For example, sets of patches 1210, 1211, 1212 at a lower resolution (higher context) and a set of patches at a high resolution (lower context) that will be similar to the target patches that will be processed during production (i.e., operational use). The machine learning server 816 may associate a class label for each patch from the labeled training data based at least on the corresponding portion of a respective class label mask.

The encoder-decoder architecture 700 may include, for each encoder-decoder 300*a-d*, one or more neural networks ("networks") feature extraction and pixel classification. The machine learning server 816 (FIG. 8) may train the machine learning model, which may include training of the individual encoder-decoder architecture 700. Each encoder-decoder 300 is trained separately, and the weights of their neural networks can be set independently of each other. During training of the machine learning model, the machine learning server 816 may set the initial weights in the neural networks of the encoder-decoders to randomly or pseudo-randomly generated values. The machine learning server 816 inputs data to the machine learning model based on an image from the training data and predicts result(s)—in this case a classification for the image, such as individual classifications for each patch. The machine learning server 816 may compare the predicted classification(s) with the expected result(s) from the labeled training data 1204. This portion of the training process to predict a result is depicted as the forward activity 1216.

Following the forward activity 1216, the machine learning server 816 may calculate an error by comparing the predicted classification with the expected class label. The machine learning server may propagate the error through the neural networks and adjust the weights of each of the encoder-decoder networks. This portion of the training process to propagate the error through the networks of the machine learning model is depicted as the backward activity 1218.

As described herein, the machine learning server 816 may train each encoder-decoder network with individual patches from the training data 1202, 1204. An exemplary encoder-decoder network may include, but is not limited to, a convolutional neural network (CNN). The machine learning server 816 may train each encoder-decoder 300*a-d* network with a sequence of patches from the training data 1202, 1204, such as the patches 1210, 1211, 1212, 1213 from an image file. An exemplary sequence of patches from an image may include iterating through the patches from an image file from left to right and top to bottom, or vice-versa. Other sequences or patterns may be used to iterate through the patches. Another exemplary sequence of patches from an image may include iterating through the patches from an image file such that each subsequent patch is adjacent to a previously provided patch. The machine learning server 816 may further train encoder-decoders based at least in part on a sequential and spatial relationship of at least some of the patches from a same image since the patches may be provided to portions of the machine learning model in a sequence. In various embodiments, the machine learning server 816 may train the encoder-decoders architecture 700 to output an overall classification from the individual classifications.

The machine learning server 816 may perform the forward and backward activities 1216, 1218 for multiple images in the training data, such as the entire training data set 1202, 1204. In various embodiments, the machine learning server 816 may perform the forward and backward activities 1216 on the entire training data set 1202, 1204 for multiple passes, which may be referred to herein as "epochs." The machine learning server 816 may continue training the machine learning model until a certain threshold is met, such as a threshold number of passes through the training data 1202, 1204, a threshold level of error has been satisfied, loss begins to increase, and/or accuracy begins to decrease. At the end of the training process, the machine learning server 816 has determined the weights 1220 for the machine learning model.

Figure 13:
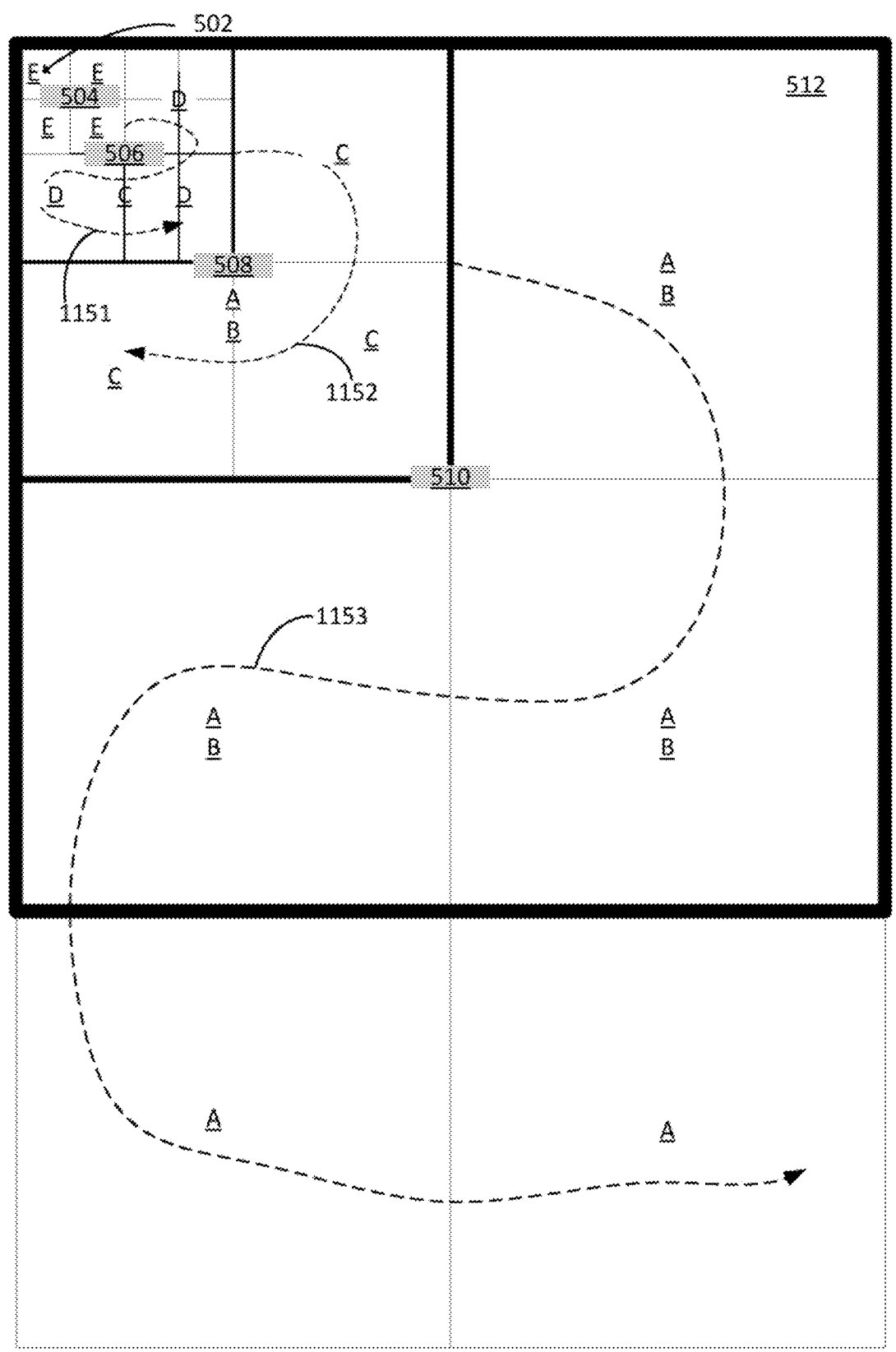
FIG. 13 illustrates an example of processing paths for semantic segmentation of a multi-resolution image.

FIG. 13 illustrates an example of processing paths for semantic segmentation of a set of MR Images such as could be included in a WSI 512 as described in reference to FIG. 5. In this example, images are a set of MR Images which includes a rectangular high-context image 510 of a first resolution. In this example, the set of MR Images also includes images 508, 506, 504, and 502, that are outlined in FIG. 12, that are increasingly of a higher resolution and lower context (as well as corresponding images of each resolution that are not individually delineated/shown in FIG. 13). Image 502 is a target image of the highest resolution and lowest context. The decoder portion of the context image processing encoder-decoders do not run at inference time (e.g., production), only during training. The encoder and decoder portions of the target image processing encoder-decoder runs at inference time. To improve computational cost and runtime efficiency, an image processing procedure can be used to designate the order of processing of the images by encoder-decoders.

In an example, a largest context lowest resolution image is first processed (for example, image 510) by a first encoder-decoder to determine feature information ("first feature information") within the image, and the first feature information is stored. The first encoder-decoder was trained using an enriched dataset including images having the resolution of image 510. Then, each of the portions (tile) B of image 510 (for example, image 508) are processed by one or more second encoder-decoders trained to determine feature information within the image ("second feature information"), and the second feature information is stored. For example, along path 1153. Each second encoder-decoder was trained using an enriched data set including images having the resolution of image 508.

Each of the portions C of image 508 (for example, image 506) are processed by one or more third encoder-decoders trained to determine feature information ("third feature information") within the image, and the third feature information is stored. For example, along path 1152. Each third encoder-decoder is trained using an enriched data set including images having the resolution of image 506. Then, each of the portions D of image 506 (for example, image 504) are processed by one or more fourth encoder-decoders trained to determine feature information ("fourth feature information") within the image, and the fourth feature information is stored. For example, along path 1151. Each fourth encoder-decoder is trained using an enriched data set including images having the resolution of image 504. Each of the portions E of image 504 (for example, image 502) are then processed by one or more fifth encoder-decoders to determine pixel classification information within the images. In addition, the one or more fifth encoder-decoders access/retrieve the feature information generated by the first, second, third and fourth encoder-decoders (that is, feature information from two or more encoder-decoders that is generated based on higher context images) and use it to determine the pixel classification information. The fifth encoder-decoders are trained to determine classification information using an enriched data set including images having the resolution of image 502.

In other words, in this example, the first branch (encoder-decoder) of the model is passed in image 510. That image is run through the encoder half of the model. The encoded features (first feature information) are then temporarily stored. the second branch of the model runs the encoder half of the model on image 508, and stores the temporary features (second feature information). This is repeated for the third branch with image 506 (third feature information is stored), and the fourth branch with image 504 (fourth feature information is stored). Then, the fifth branch processes image 502 (highest resolution image) with its encoder portion and produces feature information (fifth feature information). Then the decoder portion of the fifth branch runs using the feature information produced by the first, second, third, fourth and fifth branches and creates a prediction of classifications. The fifth branch repeats this process for all tiles E of image 504. The fourth branch runs on another tile D of image 506 and then the fifth branch repeats its process for the 4 new tiles that are in tile D. This process is repeated for all of the tiles D before the third branch processes for the next tile C, and all of fifth branch and the fourth branch processing is repeated of the new image patches. All of this process is repeated for the other branches until the fifth branch has processes every relevant image patch in the image. Non-tissue portions of the image do not need to be processed. (don't need to run on non-tissue portions of the image) in the image.

Figure 14:
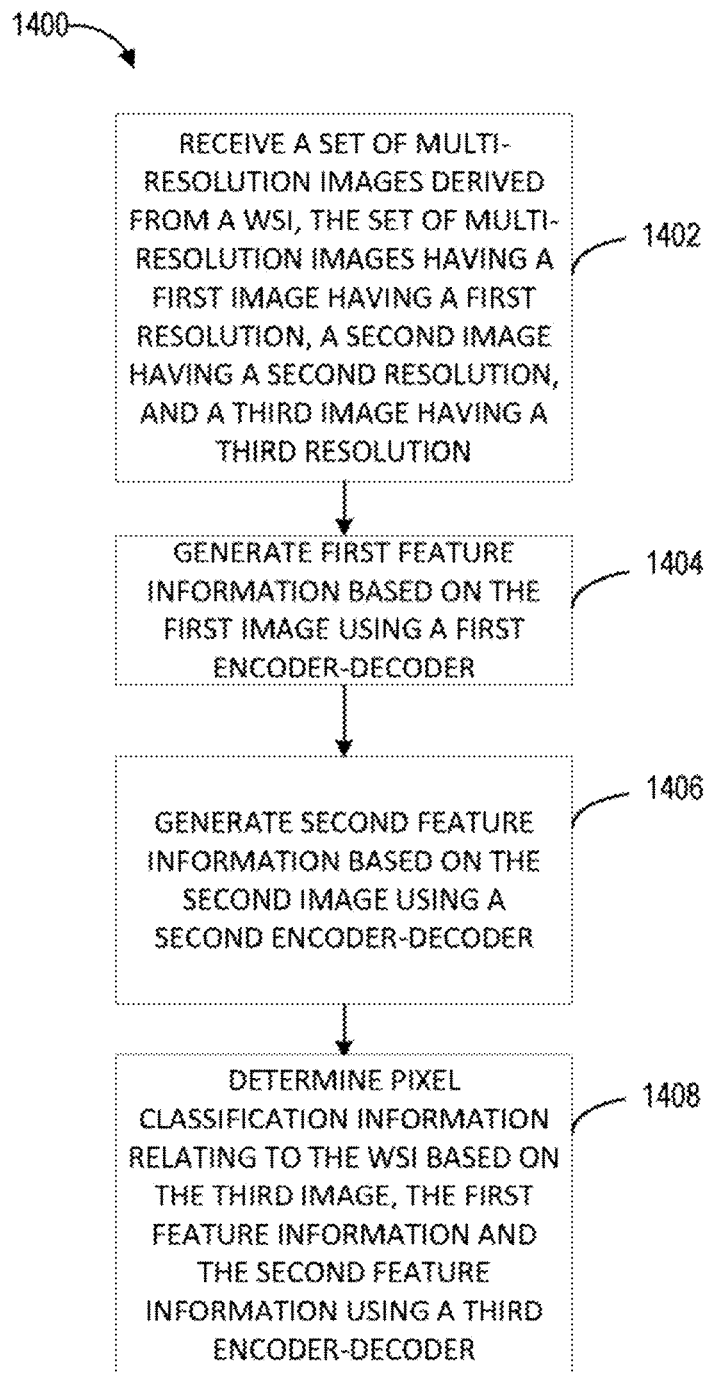
FIG. 14 is an example of an embodiment of a process for semantic segmentation of multi-resolution images.
Figure 15:
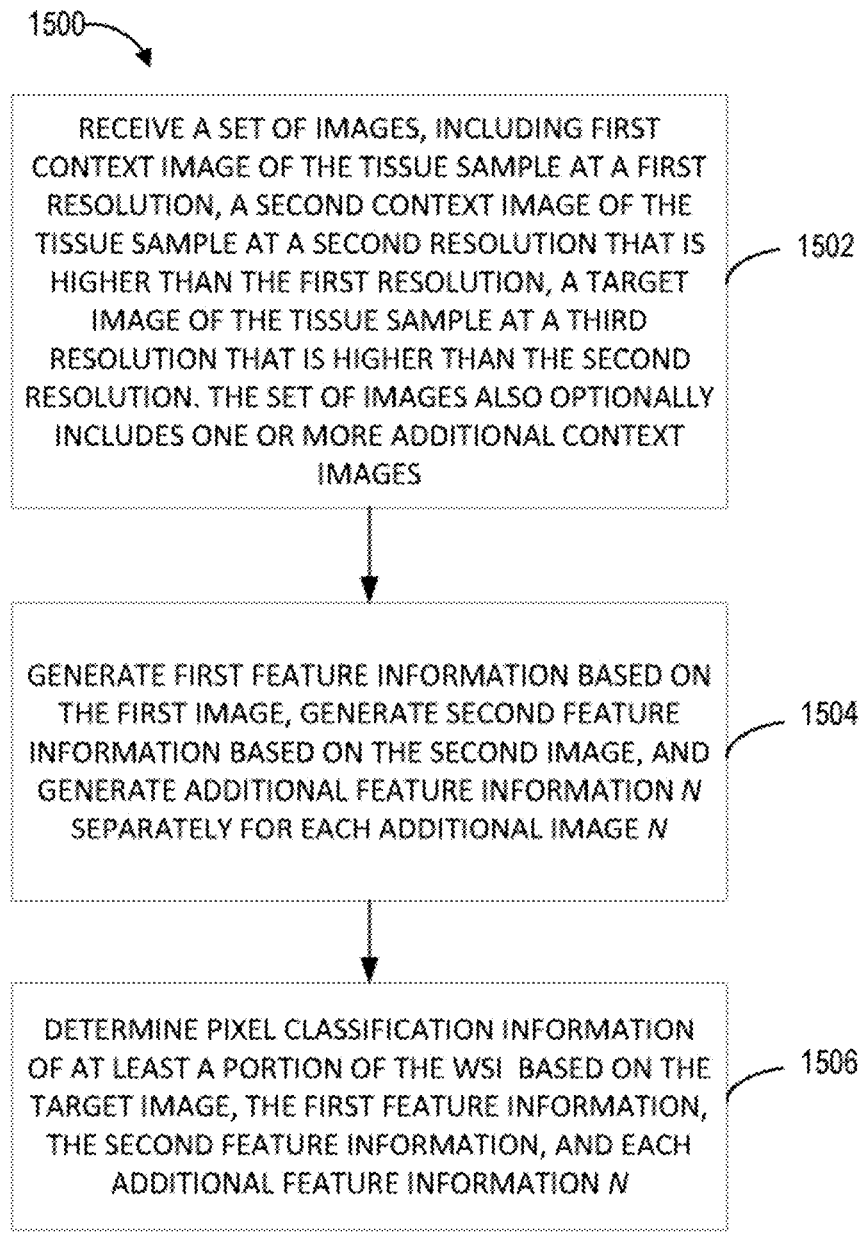
FIG. 15 is an example of another embodiment of a process for semantic segmentation of multi-resolution images.

FIG. 14 is an example of a method 1400 for determining pixel classifications of at least a portion of a whole slide image (WSI) using a set of images depicting at least a portion of the WSI. This method can be performed using one or more of the components of the systems described herein, for example, it can be performed by one or more computer hardware processors executing program instructions stored on a non-transitory computer medium. At block 1402, the method 1400 receives a set of multi-resolution images derived from the WSI depicting at least a portion of a tissue sample. The set of multi-resolution images has at least a first image of the tissue sample at a first resolution, a second image of the tissue sample at a second resolution that is higher than the first resolution, and a third image of the tissue sample at a third resolution that is higher than the second resolution, the first, second, and third images depicting at least a portion of a same area of the tissue sample. At block 1404 the method 1400 generates first feature information based on the first image using a first encoder-decoder. At block 1406, the method 1400 generates second feature information based on the second image and at least a portion of the first feature information using a second encoder-decoder. At block 1408 the method 1400 determines pixel classification information relating to the WSI based on the third image and at least a portion of the second feature information using a third encoder-decoder.

FIG. 15 is an example of another embodiment of a process 1500 for semantic segmentation of multi-resolution images. At block 1502 the process 1500 receives a set of images. The set of images includes a first context image of the tissue sample at a first resolution, a second context image of the tissue sample at a second resolution that is higher than the first resolution, a target image of the tissue sample at a third resolution that is higher than the second resolution. The set of images also optionally includes one or more additional context images n where n is an integer, wherein when n=1 the additional context image 1 has a resolution higher than the resolution of the second context image, wherein when n>1 each additional context image n has a resolution higher than the resolution of the additional image n−1, and wherein the first context image, second context image, target image, and each additional image n depict at least a portion of a same area of the tissue sample.

At block 1504 the process 1500 generates first feature information based on the first image, generates second feature information based on the second image, and generates additional feature information n separately for each additional image n.

At block 1506 process 1500 determines pixel classification information of at least a portion of the WSI based on the target image, the first feature information, the second feature information, and each additional feature information n. As described herein, this process can be performed by one or more computer hardware processors executing program instructions stored on a non-transitory computer medium.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the disclosure should not be taken to imply that the terminology is being re-defined herein to be restricted to including any specific characteristics of the features or aspects of the technology with which that terminology is associated.

It will be appreciated by those skilled in the art that various modifications and changes can be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures can be combined, interchanged or excluded from other embodiments. Additionally, further illustrations of potential implementations and variations are provided in the clauses below, which relate to various non-exhaustive ways in which the teachings herein may be combined or applied.

Clause 1

An apparatus for determining pixel classification information using a set of images depicting at least some of a whole slide image (WSI) of a stained tissue sample, comprising: a non-transitory computer storage medium configured to store executable instructions, and one or more hardware processors in communication with the computer storage medium, wherein the executable instructions, when executed by the one or more hardware processors, configure the one or more hardware processors to generate first feature information based on a first context image of the tissue sample at a first resolution; generate additional feature information n separately for one or more additional context images n where n is an integer, wherein when n=1 the additional context image 1 has a resolution 1 which is higher than the first resolution, wherein when n>1 each additional context image n has a resolution n which is higher than the resolution of the additional context image n−1, and wherein the first context image, target image, and each additional context image n depicts at least a portion of a same area of the tissue sample; and determine pixel classification information of at least a portion of the WSI based on a target image of the tissue sample at a second resolution that is higher than the highest resolution of any of the one or more additional context images n, the first feature information, and each additional feature information n.

Clause 2

The apparatus of clause 1, wherein the executable instructions, when executed by the one or more hardware processors, further configure the one or more hardware processors to: generate the first feature information using a first encoder-decoder trained for feature detection and pixel classification using an enriched dataset including images of the first resolution, wherein the first feature information is an intermediary output of the first encoder-decoder, generate each of the additional feature information n using a encoder-decoder n trained for feature detection and pixel classification using an enriched dataset including images of the resolution n, wherein the additional feature information n is an intermediary output of the encoder-decoder n, determine the pixel classification information of at least a portion of the WSI based on the target image using a target encoder-decoder trained for feature detection and pixel classification using an enriched data set that includes target images.

Clause 3

The apparatus of clause 2, wherein the executable instructions, when executed by the one or more hardware processors, configure the one or more hardware processors to: generate the first feature information prior to generating a final output from the first encoder-decoder, and
for each additional feature information n, generating the additional feature information n prior to generating a final output of a pixel classification from each encoder-decoder n.

Clause 4

The apparatus of clause 2, wherein each encoder-decoder includes multiple encoder layers and decoder layers.

Clause 5

The apparatus of clause 4, wherein the number of encoder layers of at least two of the encoder-decoders are different.

Clause 6

The apparatus of clause 4, wherein the number of decoder layers of at least two of the encoder-decoders are different.

Clause 7

The apparatus of any preceding clause, wherein the first, and $n^{th}$ images depict spatially concentric areas of the tissue sample, or spatially non-concentric areas of the tissue sample.

Clause 8

The apparatus of any preceding clause, wherein the first, second and nth images depict spatially non-concentric areas of the tissue sample.

Clause 9

The apparatus of any of clauses 2 to 6, wherein the executable instructions, when executed by the one or more hardware processors, further configure the one or more hardware processors to store the first, and additional feature information n, and provide the first, and additional feature information n to the target encoder-decoder.

Clause 10

The apparatus of any of clauses 2 to 6, where the target encoder-decoder includes a layer that processes image data having the same resolution as the resolution of the first context image, and each of the additional context images n.

Clause 11

The apparatus of any of clauses 2 to 6, wherein each encoder-decoder includes a convolutional neural network.

Clause 12

The apparatus of clause 11, wherein each encoder-decoder includes a convolutional neural network trained using an enriched dataset including images of the same resolution as the images the encoder-decoder is used to inference.

The apparatus of clause 11, wherein each encoder-decoder includes a convolution neural network trained using an enriched dataset including only images of the same resolution as the images the encoder-decoder is used to inference.

Clause 14

The apparatus of clause 1, wherein: the first context image is comprised by a set of first context images, wherein: each image from the set of first context images depicts a different portion of the tissue sample at the first resolution; and each of the one or more additional context images n is comprised by a set of context images n wherein: for each set of context images n, each image in that set has the resolution n; the set of context images 1 comprises a plurality of subsets of context images 1, wherein each subset from the plurality of subsets of context images 1 corresponds to a different image from the set of first context images; for each subset from the plurality of subsets of context images 1, each image in that subset depicts a different portion of the portion of the tissue sample depicted in the image from the set of first context images which corresponds to that subset of context images 1; when n>1: the set of context images n comprises a plurality of subsets of context images n, wherein each subset from the plurality of subsets of context images n corresponds to a different image from the set of context images n–1; and for each subset from the plurality of subsets of context images n, each image in that subset depicts a different portion of the portion of the tissue sample depicted in the image from the set of context images n–1 which corresponds to that subset of context images n; the target image of the tissue sample is comprised by a set of target images, wherein: the set of target images comprises a plurality of subsets of target images, wherein each subset from the plurality of subsets of target images corresponds to a different image from the set of context images n; for each subset from the plurality of subsets of target images, each image in that subset depicts a different portion of the portion of the tissue sample depicted in the image from the set of context images n which corresponds to that subset of target images; and for each image from the set of target images, the portion of the tissue sample depicted in that image is depicted in that image at the second resolution; the executable instructions, when executed by the one or more hardware processors, configure the one or more hardware processors to: for each subset of context images 1, generate first feature information based on the image from the set of first context images which corresponds to that subset before generating additional feature information 1 based on any of the images from that subset; when n>1, for each subset of context images n, generate additional feature information n–1 based on the image from the from the set of context images n–1 which corresponds to that subset before generating additional feature information n based on any of the images from that subset; for each subset of target images, before determining pixel classification information based on any image from that subset, generate additional feature information n based on the image from the set of context images n which corresponds to that subset; and perform a pixel classification information determination procedure comprising, for each image from the set of target images, determining pixel classification information based on that image from the set of target images; and determining pixel classification information of at least the portion of the WSI based on the target image, the first feature information, and each additional feature information n is comprised by the pixel classification information determination procedure.

Clause 15

A non-transitory computer readable medium for determining pixel classification of at least a portion of a whole slide image (WSI) using a set of images depicting at least a portion of the WSI, the computer readable medium having program instructions for causing a hardware processor to perform a method of: receiving a set of images including: a first context image of the tissue sample at a first resolution, a target image of the tissue sample at a second resolution that is higher than the first resolution, and one or more additional context images n where n is an integer, wherein when n=1 the additional context image 1 has a resolution higher than the resolution of the first context image, wherein when n>1 each additional context image n has a resolution higher than the resolution of the additional image n–1, and wherein the first context image, target image, and each additional image n depict at least a portion of a same area of the tissue sample; generating first feature information based on the first context image; generating additional feature information n separately for each additional image n; and determining pixel classification information of at least a portion of the WSI based on the target image, the first feature information and each additional feature information n.

Clause 16

The non-transitory computer readable medium of clause 15, wherein the first feature information is generated prior to generating a final output from the first encoder-decoder process, and wherein the additional feature information n is generated prior to generating a final output of a pixel classification from each encoder-decoder n.

Clause 17

The non-transitory computer readable medium of clause 15, wherein each encoder-decoder includes multiple encoder layers and decoder layers.

Clause 18

The non-transitory computer readable medium of clause 18, wherein the number of encoder layers of at least two of the encoder-decoders are different.

Clause 19

The non-transitory computer readable medium of clause 18, wherein the number of decoder layers of at least two of the encoder-decoders processes are different.

Clause 20

A method for determining pixel classification of at least a portion of a whole slide image (WSI) using a set of images depicting at least a portion of the WSI, the method being performed by a computing system and comprising the steps of: receiving a set of images including: a first context image of the tissue sample at a first resolution, a target image of the tissue sample at a second resolution that is higher than the first resolution, and one or more additional context images n where n is an integer, wherein when n=1 the additional context image 1 has a resolution higher than the resolution of the first context image, wherein when n>1 each additional context image n has a resolution higher than the resolution of the additional image n–1, and wherein the first context image, target image, and each additional image n depict at least a portion of a same area of the tissue sample; generating first feature information based on the first context image using a first encoder-decoder; generating additional feature information n separately for each additional image n using an encoder-decoder n; and determining pixel classification information of at least a portion of the WSI based on the target image, the first feature information and each additional feature information n, wherein the method is performed by one or more computer hardware processors executing program instructions stored on a non-transitory computer medium.

Clause 21

The method of clause 20, wherein the method comprises: generating the first feature information using a first encoder-decoder trained for feature detection and pixel classification using an enriched dataset including images of the first resolution, wherein the first feature information is an intermediary output of the first encoder-decoder, generating each of the additional feature information n using a encoder-decoder n trained for feature detection and pixel classification using an enriched dataset including images of the resolution n, wherein the additional feature information n is an intermediary output of the encoder-decoder n, determining the pixel classification information of at least a portion of the WSI based on the target image using a target encoder-decoder trained for feature detection and pixel classification using an enriched data set that includes target images.

Clause 22

The method of clause 20, wherein: the first context image is comprised by a set of first context images, wherein: each image from the set of first context images depicts a different portion of the tissue sample at the first resolution; and each of the one or more additional context images n is comprised by a set of context images n wherein: for each set of context images n, each image in that set has the resolution n; the set of context images 1 comprises a plurality of subsets of context images 1, wherein each subset from the plurality of subsets of context images 1 corresponds to a different image from the set of first context images; for each subset from the plurality of subsets of context images 1, each image in that subset depicts a different portion of the portion of the tissue sample depicted in the image from the set of first context images which corresponds to that subset of context images 1; when n>1: the set of context images n comprises a plurality of subsets of context images n, wherein each subset from the plurality of subsets of context images n corresponds to a different image from the set of context images n−1; and for each subset from the plurality of subsets of context images n, each image in that subset depicts a different portion of the portion of the tissue sample depicted in the image from the set of context images n−1 which corresponds to that subset of context images n; the target image of the tissue sample is comprised by a set of target images, wherein: the set of target images comprises a plurality of subsets of target images, wherein each subset from the plurality of subsets of target images corresponds to a different image from the set of context images n; for each subset from the plurality of subsets of target images, each image in that subset depicts a different portion of the portion of the tissue sample depicted in the image from the set of context images n which corresponds to that subset of target images; and for each image from the set of target images, the portion of the tissue sample depicted in that image is depicted in that image at the second resolution; the method comprises: for each subset of context images 1, generate first feature information based on the image from the set of first context images which corresponds to that subset before generating additional feature information 1 based on any of the images from that subset; when n>1, for each subset of context images n, generate additional feature information n−1 based on the image from the from the set of context images n−1 which corresponds to that subset before generating additional feature information n based on any of the images from that subset; for each subset of target images, before determining pixel classification information based on any image from that subset, generate additional feature information n based on the image from the set of context images n which corresponds to that subset; and perform a pixel classification information determination procedure comprising, for each image from the set of target images, determining pixel classification information based on that image from the set of target images; and determining pixel classification information of at least the portion of the WSI based on the target image, the first feature information, and each additional feature information n is comprised by the pixel classification information determination procedure.

With respect to the use of substantially any plural and/or singular terms herein, those having skill in the art can translate from the plural to the singular and/or from the singular to the plural as is appropriate to the context and/or application. The various singular/plural permutations can be expressly set forth herein for sake of clarity.

Directional terms used herein (e.g., top, bottom, side, up, down, inward, outward, etc.) are generally used with reference to the orientation shown in the figures and are not intended to be limiting. For example, the top surface described above can refer to a bottom surface or a side surface. Thus, features described on the top surface may be included on a bottom surface, a side surface, or any other surface.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The term "comprising" as used herein is synonymous with "including," "containing," or "characterized by," and is inclusive or open-ended and does not exclude additional, unrecited elements or method steps.

The above description discloses several methods and materials of the present invention(s). This invention(s) is susceptible to modifications in the methods and materials, as well as alterations in the fabrication methods and equipment. Such modifications will become apparent to those skilled in the art from a consideration of this disclosure or practice of the invention(s) disclosed herein. Consequently, it is not intended that this invention(s) be limited to the specific embodiments disclosed herein, but that it cover all modifications and alternatives coming within the true scope and spirit of the invention(s) as embodied in the attached claims.

What is claimed is:

1. An apparatus for determining pixel classification information using a set of images depicting at least some of a whole slide image (WSI) of a stained tissue sample, comprising:
a non-transitory computer storage medium configured to store executable instructions, and
one or more hardware processors in communication with the computer storage medium, wherein the executable instructions, when executed by the one or more hardware processors, configure the one or more hardware processors to
generate first feature information based on a first context image of the tissue sample at a first resolution;
generate additional feature information n separately for one or more additional context images n where n is an integer, wherein when n=1 the additional context image 1 has a resolution 1 which is higher than the first resolution, wherein when n>1 each additional context image n has a resolution n which is higher than the resolution of the additional context image n−1, and wherein the first context image, target image, and each additional context image n depicts at least a portion of a same area of the tissue sample; and
determine pixel classification information of at least a portion of the WSI based on a target image of the tissue sample at a second resolution that is higher than the highest resolution of any of the one or more additional context images n, the first feature information, and each additional feature information n.

2. The apparatus of claim 1, wherein the executable instructions, when executed by the one or more hardware processors, further configure the one or more hardware processors to:
generate the first feature information using a first encoder-decoder trained for feature detection and pixel classification using an enriched dataset including images of the first resolution, wherein the first feature information is an intermediary output of the first encoder-decoder,
generate each of the additional feature information n using a encoder-decoder n trained for feature detection and pixel classification using an enriched dataset including images of the resolution n, wherein the additional feature information n is an intermediary output of the encoder-decoder n,
determine the pixel classification information of at least a portion of the WSI based on the target image using a target encoder-decoder trained for feature detection and pixel classification using an enriched data set that includes target images.

3. The apparatus of claim 2, wherein the executable instructions, when executed by the one or more hardware processors, configure the one or more hardware processors to:
generate the first feature information prior to generating a final output from the first encoder-decoder, and
for each additional feature information n, generating the additional feature information n prior to generating a final output of a pixel classification from each encoder-decoder n.

4. The apparatus of claim 2, wherein each encoder-decoder includes multiple encoder layers and decoder layers.

5. The apparatus of claim 4, wherein the number of encoder layers of at least two of the encoder-decoders are different.

6. The apparatus of claim 4, wherein the number of decoder layers of at least two of the encoder-decoders are different.

7. The apparatus of claim 2, wherein the executable instructions, when executed by the one or more hardware processors, further configure the one or more hardware processors to store the first, and additional feature information n, and provide the first, and additional feature information n to the target encoder-decoder.

8. The apparatus of claim 2, where the target encoder-decoder includes a layer that processes image data having the same resolution as the resolution of the first context image, and each of the additional context images n.

9. The apparatus of claim 2, wherein each encoder-decoder includes a convolutional neural network.

10. The apparatus of claim 9, wherein each encoder-decoder includes a convolutional neural network trained using an enriched dataset including images of the same resolution as the images the encoder-decoder is used to inference.

11. The apparatus of claim 9, wherein each encoder-decoder includes a convolution neural network trained using an enriched dataset including only images of the same resolution as the images the encoder-decoder is used to inference.

12. The apparatus of claim 1, wherein the first, and $n^{th}$ images depict spatially concentric areas of the tissue sample, or spatially non-concentric areas of the tissue sample.

13. The apparatus of claim 1, wherein the first, second and $n^{th}$ images depict spatially non-concentric areas of the tissue sample.

14. The apparatus of claim 1, wherein:
the first context image is comprised by a set of first context images, wherein:
each image from the set of first context images depicts a different portion of the tissue sample at the first resolution; and
each of the one or more additional context images n is comprised by a set of context images n wherein:
for each set of context images n, each image in that set has the resolution n;
the set of context images 1 comprises a plurality of subsets of context images 1, wherein each subset from the plurality of subsets of context images 1 corresponds to a different image from the set of first context images;
for each subset from the plurality of subsets of context images 1, each image in that subset depicts a different portion of the portion of the tissue sample depicted in the image from the set of first context images which corresponds to that subset of context images 1;
when n>1:
the set of context images n comprises a plurality of subsets of context images n, wherein each subset from the plurality of subsets of context images n corresponds to a different image from the set of context images n−1; and
for each subset from the plurality of subsets of context images n, each image in that subset depicts a different portion of the portion of the tissue sample depicted in the image from the set of context images n−1 which corresponds to that subset of context images n;

the target image of the tissue sample is comprised by a set of target images, wherein:

the set of target images comprises a plurality of subsets of target images, wherein each subset from the plurality of subsets of target images corresponds to a different image from the set of context images n;

for each subset from the plurality of subsets of target images, each image in that subset depicts a different portion of the portion of the tissue sample depicted in the image from the set of context images n which corresponds to that subset of target images; and for each image from the set of target images, the portion of the tissue sample depicted in that image is depicted in that image at the second resolution;

the executable instructions, when executed by the one or more hardware processors, configure the one or more hardware processors to:

for each subset of context images 1, generate first feature information based on the image from the set of first context images which corresponds to that subset before generating additional feature information 1 based on any of the images from that subset;

when n>1, for each subset of context images n, generate additional feature information n−1 based on the image from the from the set of context images n−1 which corresponds to that subset before generating additional feature information n based on any of the images from that subset;

for each subset of target images, before determining pixel classification information based on any image from that subset, generate additional feature information n based on the image from the set of context images n which corresponds to that subset; and perform a pixel classification information determination procedure comprising, for each image from the set of target images, determining pixel classification information based on that image from the set of target images; and determining pixel classification information of at least the portion of the WSI based on the target image, the first feature information, and each additional feature information n is comprised by the pixel classification information determination procedure.

15. A non-transitory computer readable medium for determining pixel classification of at least a portion of a whole slide image (WSI) using a set of images depicting at least a portion of the WSI, the computer readable medium having program instructions for causing a hardware processor to perform a method of:

receiving a set of images including:

a first context image of the tissue sample at a first resolution, a target image of the tissue sample at a second resolution that is higher than the first resolution, and one or more additional context images n where n is an integer, wherein when n=1 the additional context image 1 has a resolution higher than the resolution of the first context image, wherein when n>1 each additional context image n has a resolution higher than the resolution of the additional image n−1, and wherein the first context image, target image, and each additional image n depict at least a portion of a same area of the tissue sample;

generating first feature information based on the first context image using a first encoder-decoder;

generating additional feature information n separately for each additional image n using an encoder-decoder n; and determining pixel classification information of at least a portion of the WSI based on the target image, the first feature information and each additional feature information n, wherein the method is performed by one or more computer hardware processors executing program instructions stored on a non-transitory computer medium.

16. The non-transitory computer readable medium of claim 15, wherein the method comprises:

generating the first feature information using a first encoder-decoder trained for feature detection and pixel classification using an enriched dataset including images of the first resolution, wherein the first feature information is an intermediary output of the first encoder-decoder, generating each of the additional feature information n using a encoder-decoder n trained for feature detection and pixel classification using an enriched dataset including images of the resolution n, wherein the additional feature information n is an intermediary output of the encoder-decoder n, and determining the pixel classification information of at least a portion of the WSI based on the target image using a target encoder-decoder trained for feature detection and pixel classification using an enriched data set that includes target images.

17. The non-transitory computer readable medium of claim 15, wherein:

the first context image is comprised by a set of first context images, wherein:

each image from the set of first context images depicts a different portion of the tissue sample at the first resolution; and each of the one or more additional context images n is comprised by a set of context images n wherein:

for each set of context images n, each image in that set has the resolution n;

the set of context images 1 comprises a plurality of subsets of context images 1, wherein each subset from the plurality of subsets of context images 1 corresponds to a different image from the set of first context images;

for each subset from the plurality of subsets of context images 1, each image in that subset depicts a different portion of the portion of the tissue sample depicted in the image from the set of first context images which corresponds to that subset of context images 1;

when n>1:

the set of context images n comprises a plurality of subsets of context images n, wherein each subset from the plurality of subsets of context images n corresponds to a different image from the set of context images n−1; and for each subset from the plurality of subsets of context images n, each image in that subset depicts a different portion of the portion of the tissue sample depicted in the image from the set of context images n−1 which corresponds to that subset of context images n;

the target image of the tissue sample is comprised by a set of target images, wherein:

the set of target images comprises a plurality of subsets of target images, wherein each subset from the plurality of subsets of target images corresponds to a different image from the set of context images n;

for each subset from the plurality of subsets of target images, each image in that subset depicts a different portion of the portion of the tissue sample depicted in the image from the set of context images n which corresponds to that subset of target images; and for each image from the set of target images, the portion of the tissue sample depicted in that image is depicted in that image at the second resolution;

the method comprises:

for each subset of context images 1, generate first feature information based on the image from the set of first context images which corresponds to that subset before generating additional feature information 1 based on any of the images from that subset;

when n>1, for each subset of context images n, generate additional feature information n−1 based on the image from the from the set of context images n−1 which corresponds to that subset before generating additional feature information n based on any of the images from that subset;

for each subset of target images, before determining pixel classification information based on any image from that subset, generate additional feature information n based on the image from the set of context images n which corresponds to that subset; and perform a pixel classification information determination procedure comprising, for each image from the set of target images, determining pixel classification information based on that image from the set of target images; and determining pixel classification information of at least the portion of the WSI based on the target image, the first feature information, and each additional feature information n is comprised by the pixel classification information determination procedure.

18. A method for determining pixel classification of at least a portion of a whole slide image (WSI) using a set of images depicting at least a portion of the WSI, the method being performed by a computing system and comprising the steps of:

receiving a set of images including:
a first context image of the tissue sample at a first resolution,
a target image of the tissue sample at a second resolution that is higher than the first resolution, and
one or more additional context images n where n is an integer, wherein when n=1 the additional context image 1 has a resolution higher than the resolution of the first context image, wherein when n>1 each additional context image n has a resolution higher than the resolution of the additional image n−1, and wherein the first context image, target image, and each additional image n depict at least a portion of a same area of the tissue sample;

generating first feature information based on the first context image using a first encoder-decoder;

generating additional feature information n separately for each additional image n using an encoder-decoder n; and determining pixel classification information of at least a portion of the WSI based on the target image, the first feature information and each additional feature information n, wherein the method is performed by one or more computer hardware processors executing program instructions stored on a non-transitory computer medium.

19. The method of claim 18, wherein the method comprises:

generating the first feature information using a first encoder-decoder trained for feature detection and pixel classification using an enriched dataset including images of the first resolution, wherein the first feature information is an intermediary output of the first encoder-decoder, generating each of the additional feature information n using a encoder-decoder n trained for feature detection and pixel classification using an enriched dataset including images of the resolution n, wherein the additional feature information n is an intermediary output of the encoder-decoder n, determining the pixel classification information of at least a portion of the WSI based on the target image using a target encoder-decoder trained for feature detection and pixel classification using an enriched data set that includes target images.

20. The method of claim 18, wherein:

the first context image is comprised by a set of first context images, wherein:

each image from the set of first context images depicts a different portion of the tissue sample at the first resolution; and each of the one or more additional context images n is comprised by a set of context images n wherein:

for each set of context images n, each image in that set has the resolution n;

the set of context images 1 comprises a plurality of subsets of context images 1, wherein each subset from the plurality of subsets of context images 1 corresponds to a different image from the set of first context images;

for each subset from the plurality of subsets of context images 1, each image in that subset depicts a different portion of the portion of the tissue sample depicted in the image from the set of first context images which corresponds to that subset of context images 1;

when n>1:

the set of context images n comprises a plurality of subsets of context images n, wherein each subset from the plurality of subsets of context images n corresponds to a different image from the set of context images n−1; and for each subset from the plurality of subsets of context images n, each image in that subset depicts a different portion of the portion of the tissue sample depicted in the image from the set of context images n−1 which corresponds to that subset of context images n;

the target image of the tissue sample is comprised by a set of target images, wherein:

the set of target images comprises a plurality of subsets of target images, wherein each subset from the plurality of subsets of target images corresponds to a different image from the set of context images n;

for each subset from the plurality of subsets of target images, each image in that subset depicts a different portion of the portion of the tissue sample depicted in the image from the set of context images n which corresponds to that subset of target images; and for each image from the set of target images, the portion of the tissue sample depicted in that image is depicted in that image at the second resolution;

the method comprises:

for each subset of context images 1, generate first feature information based on the image from the set of first context images which corresponds to that subset before generating additional feature information 1 based on any of the images from that subset;

when n>1, for each subset of context images n, generate additional feature information n−1 based on the image from the from the set of context images n−1 which corresponds to that subset before generating additional feature information n based on any of the images from that subset;

for each subset of target images, before determining pixel classification information based on any image from that subset, generate additional feature information n based on the image from the set of context images n which corresponds to that subset; and perform a pixel classification information determination procedure comprising, for each image from the set of target images, determining pixel classification information based on that image from the set of target images; and determining pixel classification information of at least the portion of the WSI based on the target image, the first feature information, and each additional feature information n is comprised by the pixel classification information determination procedure.

* * * * *